(12) United States Patent
Carmi

(10) Patent No.: US 11,250,569 B2
(45) Date of Patent: Feb. 15, 2022

(54) SYSTEMS AND METHODS FOR FUNCTIONAL IMAGING FOLLOW-UP EVALUATION USING DEEP NEURAL NETWORK

(71) Applicant: GE Precision Healthcare LLC, Milwaukee, WI (US)

(72) Inventor: Raz Carmi, Haifa (IL)

(73) Assignee: GE Precision Healthcare LLC, Milwaukee, WI (US)

(*) Notice: Subject to any disclaimer, the term of this patent is extended or adjusted under 35 U.S.C. 154(b) by 186 days.

(21) Appl. No.: 16/673,715

(22) Filed: Nov. 4, 2019

(65) Prior Publication Data

US 2021/0133976 A1 May 6, 2021

(51) Int. Cl.

| | |
|---|---|
| G06T 7/00 | (2017.01) |
| G06N 3/08 | (2006.01) |
| G06N 3/04 | (2006.01) |
| G16H 30/20 | (2018.01) |
| A61B 6/00 | (2006.01) |
| A61B 6/12 | (2006.01) |
| A61B 5/00 | (2006.01) |

(52) U.S. Cl.
CPC .......... *G06T 7/0016* (2013.01); *A61B 5/7267* (2013.01); *A61B 6/12* (2013.01); *A61B 6/4057* (2013.01); *G06N 3/0454* (2013.01); *G06N 3/08* (2013.01); *G16H 30/20* (2018.01); *G06T 2207/20081* (2013.01); *G06T 2207/20084* (2013.01); *G06T 2207/30096* (2013.01); *G06T 2207/30168* (2013.01)

(58) Field of Classification Search
CPC ....... A61B 5/7267; A61B 6/12; A61B 6/4057; G06N 3/08; G06N 3/0454; G06T 7/0016; G06T 2207/20084; G06T 2207/20081; G06T 2207/30096; G06T 2207/30168; G16H 30/20; G16H 30/40
See application file for complete search history.

(56) References Cited

U.S. PATENT DOCUMENTS

| | | | |
|---|---|---|---|
| 2016/0174895 A1* | 6/2016 | Ross | G06F 17/11 600/407 |
| 2019/0244398 A1 | 8/2019 | Carmi | |
| 2020/0075154 A1* | 3/2020 | Akahori | G16H 30/20 |

OTHER PUBLICATIONS

Hoffer, E. et al., "Deep Metric Learning Using Triplet Network," Cornell University arXiv Website, Available Online at https://arxiv.org/abs/1412.6622, Available as Early as Dec. 20, 2014, 8 pages.
(Continued)

*Primary Examiner* — Brenda C Bernardi
(74) *Attorney, Agent, or Firm* — McCoy Russell LLP

(57) ABSTRACT

Various methods and systems are provided for comparison of medical scan images during functional imaging evaluation. In one example, structural similarity between a first scan image and a second scan image of a lesion may be determined by implementing a deep learning model including plurality of neural networks trained with base structures and different perturbations of base structures, and ranking structural similarity based on a selected neural network model trained with perturbations of base structures corresponding to the structural difference between the first and second scan images.

20 Claims, 13 Drawing Sheets

(56) References Cited

OTHER PUBLICATIONS

Koch, G. et al., "Siamese Neural Networks for One-shot Image Recognition," Proceedings of the 32nd International Conference on Machine Learning, Jul. 7, 2015, Lille, France, 8 pages.
Vinyals, O. et al., "Matching Networks for One Shot Learning," Cornell University arXiv Website, Available Online at https://arxiv.org/abs/1606.04080, Available as Early as Jun. 13, 2016, 12 pages.
Yan, K. et al., "Deep Lesion Graphs in the Wild: Relationship Learning and Organization of Significant Radiology Image Findings in a Diverse Large-scale Lesion Database," Cornell University arXiv Website, Available Online at https://arxiv.org/abs/1711.10535, Available as Early as Nov. 28, 2017, 15 pages.
Snell, J. et al., "Prototypical Networks for Few-shot Learning," Proceedings of the 31st Conference on Neural Information Processing Systems (NIPS 2017), Dec. 4, 2017, Long Beach, California, 11 pages.

* cited by examiner

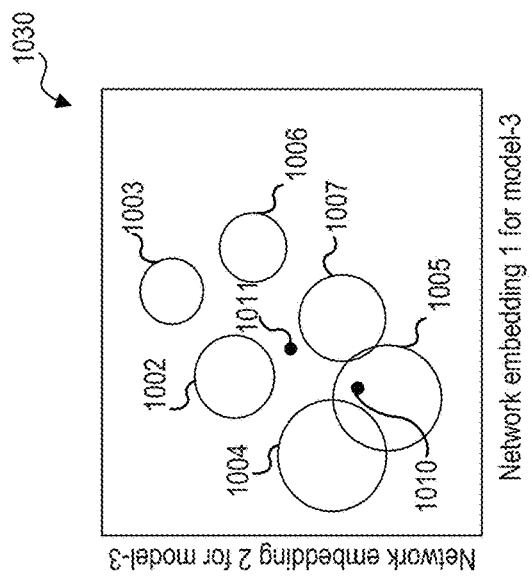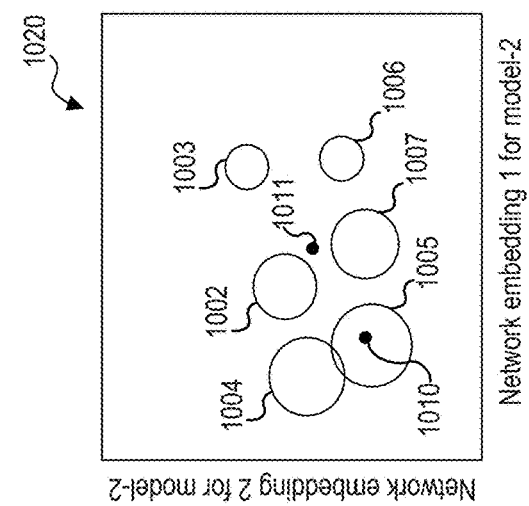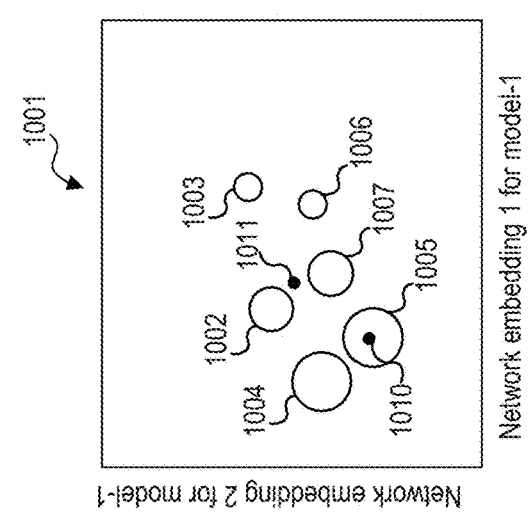
FIG. 10

SYSTEMS AND METHODS FOR FUNCTIONAL IMAGING FOLLOW-UP EVALUATION USING DEEP NEURAL NETWORK

TECHNICAL FIELD

Embodiments of the subject matter disclosed herein relate to medical imaging systems, and more particularly, to follow-up analyses using deep neural networks.

BACKGROUND

In functional medical imaging modalities, such as single-photon emission computerized tomography (SPECT) and positron-emission tomography (PET), follow-up studies may be performed involving at least two scans of the same patient acquired in different times. Such procedures can indicate, for example, the physiological response to a certain medical treatment and can help planning further patient management.

In the analysis of follow-up scans, a user/physician may typically compare image signals (values) on relevant tissue regions or organs, and assess radiotracer activity differences. For example, if an identified lesion shows significantly reduced tracer uptake in a follow-up scan after a therapy course, this may indicate good response to the therapy procedure. Otherwise, if the lesion shows increases tracer uptake, this may indicate no response and progressive disease (i.e. medical condition deterioration).

Deep learning (or 'artificial intelligence' in general) may be used in medical imaging, for example, to improve classification of learned object classes or as a technique for automatic segmentation of specific tissues and organs. However, with regard to follow-up analysis, in addition to classification and identification of lesion types, evaluation and quantification of a structural change of tracked lesions may be desired.

SUMMARY

In one embodiment, a method comprises: generating a plurality of training data sets from an un-perturbed base structure data set including a plurality of base structures, each of the plurality of training data sets having a corresponding degree of perturbation of the plurality of base structures; training each of a plurality of neural network models with each of the plurality of training data sets; and generating corresponding base structure mappings for each of the plurality of neural network models; wherein, for each of the plurality of neural networks, a corresponding distribution of the corresponding base structure mapping is based on the corresponding degree of perturbation of the corresponding training data set.

In this way, by training a deep learning model including a plurality of neural network models with a plurality of training sets with perturbations, the deep learning model may discriminate between different training structures, and also between other structures that were not used for training. Further, by generating the plurality of training data sets, the need to collect large clinical data set for model training may be significantly reduced.

The above advantages and other advantages and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 10 shows example output embeddings for different trained neural network models, according to an exemplary embodiment;

Figure 1:
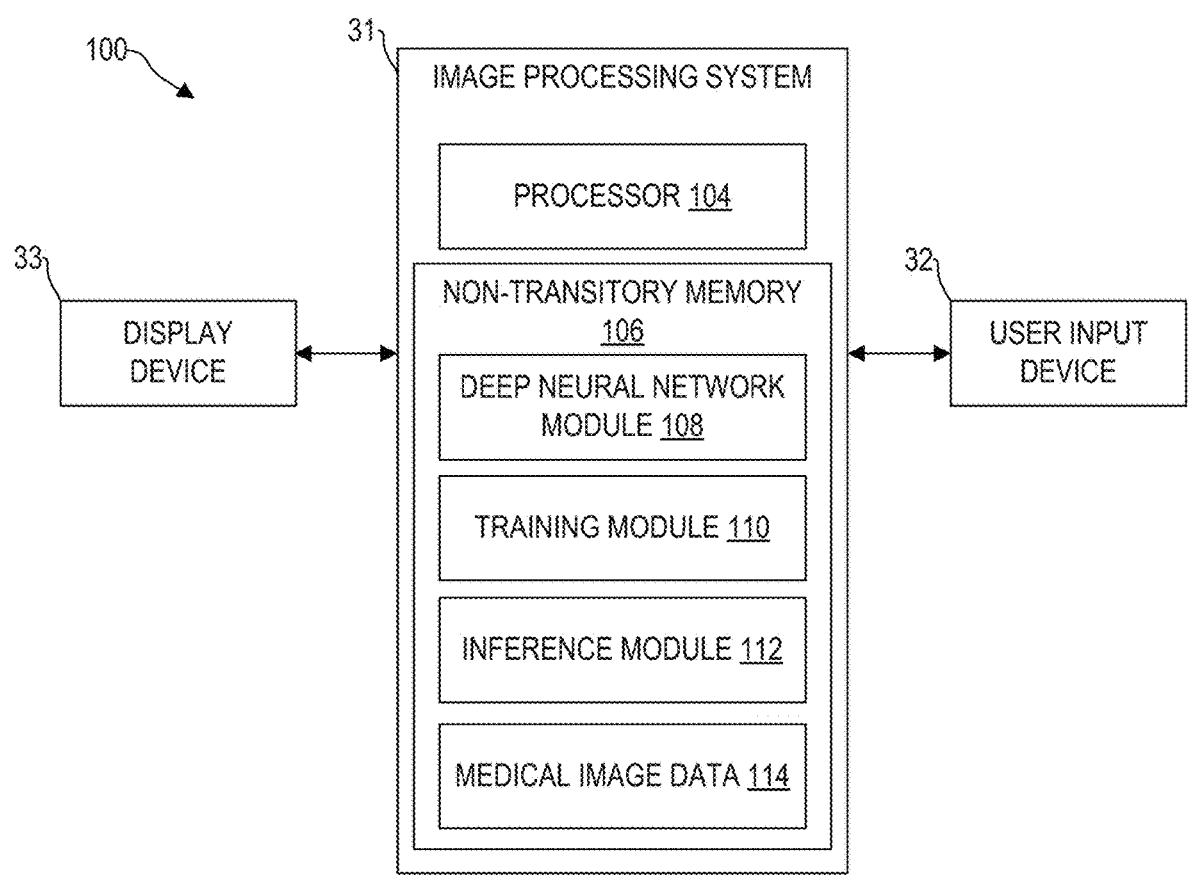
FIG. 1 is a schematic diagram illustrating an image processing system for structural comparison with deep learning, according to an exemplary embodiment.

The drawings illustrate specific aspects of the described systems and methods for comparing two or more imaged structures using a deep neural network algorithm that implements plurality of neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for evaluating structural changes to an anatomical structure, such as a lesion. In particular, systems and method are provided for constructing and testing a deep learning model that may be implemented for evaluating structural changes during follow-up studies using at least two medical scan images of the same anatomical structure of a patient acquired at different times. Such follow-up studies can indicate, for example, a physiological response to a certain medical treatment and can help planning further patient management.

In general, during analysis of follow-up scans, image signals corresponding to radiotracer uptake on relevant tissue regions or organs are compared, and a difference in radiotracer uptake activity may be evaluated. For example, if an identified lesion shows significantly reduced tracer uptake after a therapy course, this may indicate good response to the therapy procedure. Otherwise, if the lesion shows increased tracer uptake, this may indicate no response and progressive disease (i.e. medical condition deterioration).

However, the inventor has identified disadvantages with the above-mentioned approach. As an example, image signals in a relevant region may depend not only on the actual physiological staging or response of the relevant disease or medical condition, but also on other factors such as administered tracer dose, variable patient metabolism and liquids or food consumptions prior to the scan, residual tracer cleansing from the body, time passed between tracer injection to the scan, and imaging system settings and parameters.

Another important and significant aspect of lesion analysis is the morphological structures and dimensions. For example, lesion radiotracer uptake heterogeneity, lesion inhomogeneous borders or outer surface, and increased lesion sizes are linked to greater disease severity. Some common deep learning techniques such as lesion segmentation may not capture these features, especially in case of structural heterogeneity and non-uniformity. Other assisting techniques such as tissue texture analysis may provide additional information but usually they depend on many manual adjustments and empirical factors.

Furthermore, a magnitude of image signal change between the two or more follow-up scans is not, by itself, a good indication to the response assessment.

Further, previous deep learning methods for medical imaging analysis are used, for example, to improve classification of learned object classes or as a technique for automatic segmentation of specific tissues and organs, which may not provide desired lesion evaluation.

Further still, with regard to the deep learning models, the inventor has identified that variability of lesions and relevant structures may be huge. As such, sufficiently large clinical data sets needed to train a deep learning model may be difficult to obtain.

In view of the above, the inventor has identified that for lesion follow-up analysis, a combination of signal change and evaluation corresponding local structures or shapes may provide more accurate analysis. For example, if a small lesion absorbs some radiotracer concentration in a first reference scan and it is completely disappearing on the follow-up scan, this may indicate excellent response even if the tracer concentration in the reference scan is not high by itself relative to some large internal organs. In contrary, if a lesion shows high uptake signal in the reference scan and somewhat lower uptake in the follow-up scan, but exactly within the same structural distribution, this may indicate that the signal change is mostly due to the other irrelevant factors. In another example, if a lesion volume is reduced but the signal distribution within it is more heterogenous, this may indicate that the disease staging is worsen despite the lesion volume reduction. Accordingly, during lesion analysis, in order to efficiently and accurately evaluate the tracked lesions, structural change may be evaluated without necessarily classifying them into known classes.

Figure 2:
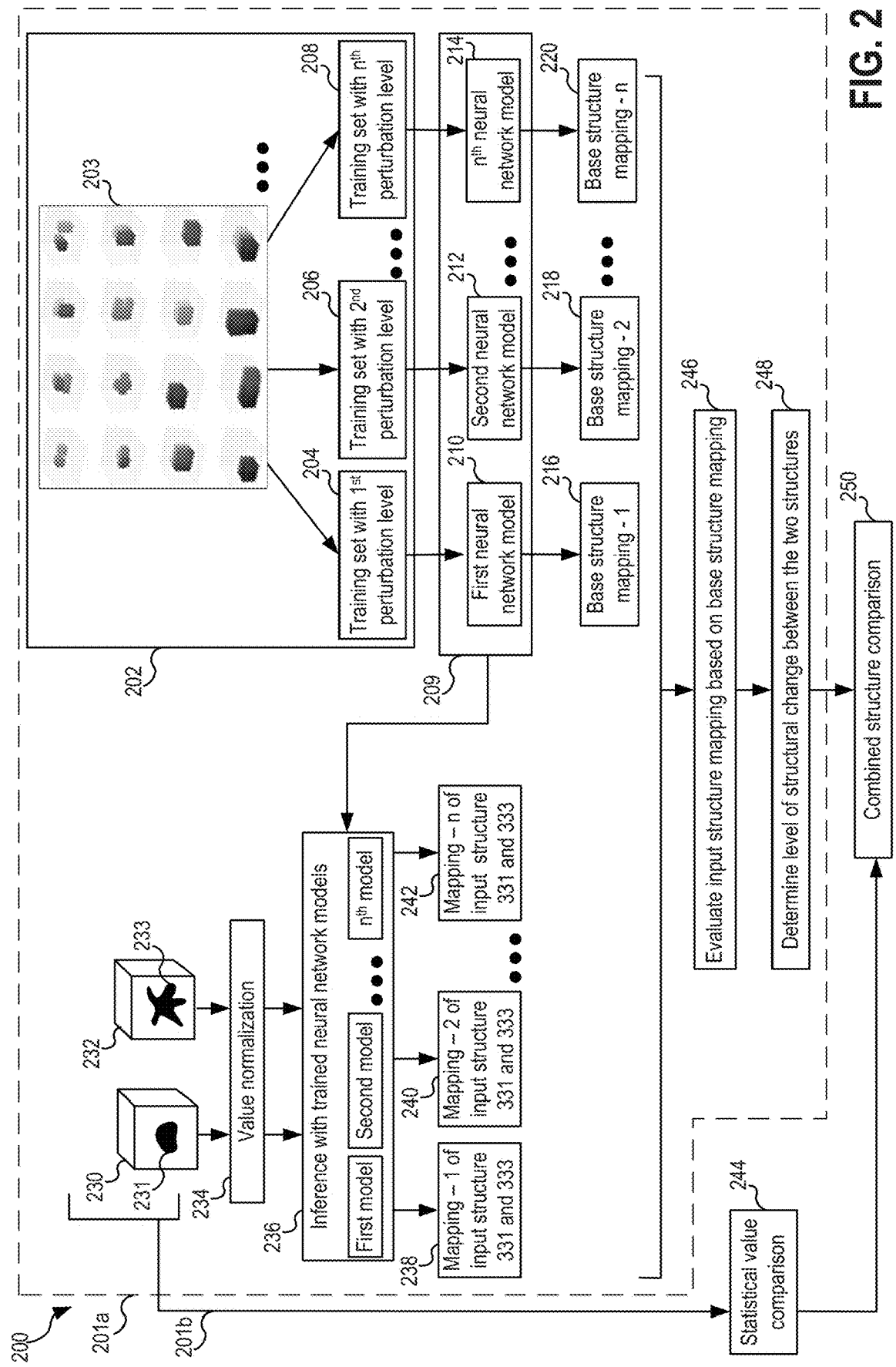
FIG. 2 is a schematic diagram illustrating a high-level deep learning model for functional imaging follow-up analysis, which can be used in the image processing system of FIG. 1, according to an exemplary embodiment.

An exemplary image processing system 100 for implementing a deep learning model in accordance with an exemplary embodiment is shown at FIG. 1. A high-level schematic of the deep learning model is illustrated at FIG. 2. The deep learning model may include a plurality of neural network models, each trained with a training set of base structures having a different perturbation level. In particular, a plurality of training sets may be generated based on an un-perturbed set of base structures. The un-perturbed set of base structures may be synthetic (that is, generated by the image processor) based on various combinations of relevant spatial frequencies and orientations, spanning a range of possible lesion structures. Each of the plurality of training sets generated based on the un-perturbed set may have a different perturbation level, where the different perturbation level of each of the plurality of training sets is based on one or more of random structural variations and image quality variations. Details of generating a plurality of training sets are described at FIG. 4. An example un-perturbed set is shown at FIG. 7A and an example data set with different types of perturbations is described at FIG. 5. Each of the plurality of training data sets may be used to train each of a plurality of neural network models. The plurality of neural network models may be trained to discriminate between different structures, and are based on convolutional neural-network. Training of each of the plurality of neural network models may be realized by algorithmic techniques based on 'few-shot learning'. Various embodiments may implement similar techniques, such as 'single-shot', 'one-shot' or 'zero-shot' learning. The advantage of such techniques is that a computational model can be trained on a relatively small set of known examples and can classify or discriminate between new input types that were not used for the training. Each of the plurality of convolutional neural network models in the deep learning model may have the same base architecture. The architecture may be any of 'Siamese networks', 'Triplet networks', 'Matching networks', 'Relation network' and 'Prototypical networks'. An example siamese network architecture that may be implemented with the deep learning model of FIG. 2 is discussed at FIG. 3. The training may include constructing a training set of plurality of different base structures, and for each base structure, generating relatively small random variations, which will be considered during the training process as belong (identical) to the same type of their un-perturbed structure. Thus, the training of each of the plurality of neural network models with the plurality of training sets may be performed with respect to the un-perturbed set of base structures such that the small random perturbations of an un-perturbed base structure will be considered as belonging to the same un-perturbed base structure and will be grouped together in a corresponding output space of each neural network model. A high level training method for the plurality of neural network models with the plurality of training data sets is described at FIG. 6. In this way, by generating a plurality of training sets and training a plurality of neural network models as discussed herein, the need to rely on large sets of clinical data for training is reduced. Further, annotation work load of large clinical data sets is reduced. Furthermore, the trained deep learning model may efficiently differentiate between anatomical structures that were not used for training.

Figure 7B:
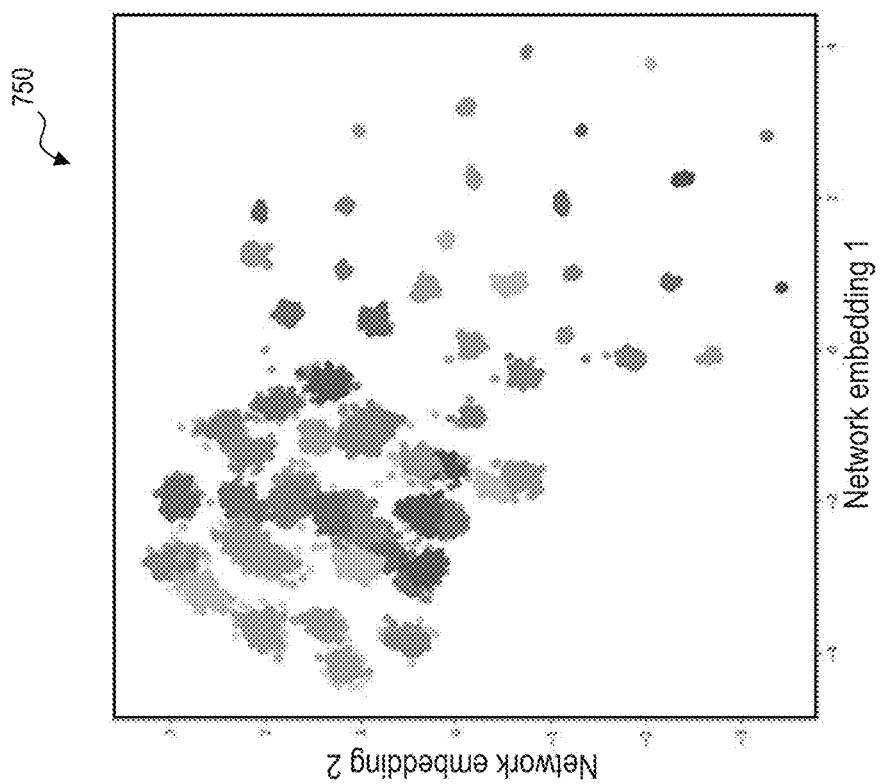
FIG. 7B shows an example output of a neural network model trained with the data set of synthetic base structures of FIG. 7A, according to an exemplary embodiment.
Figure 12:
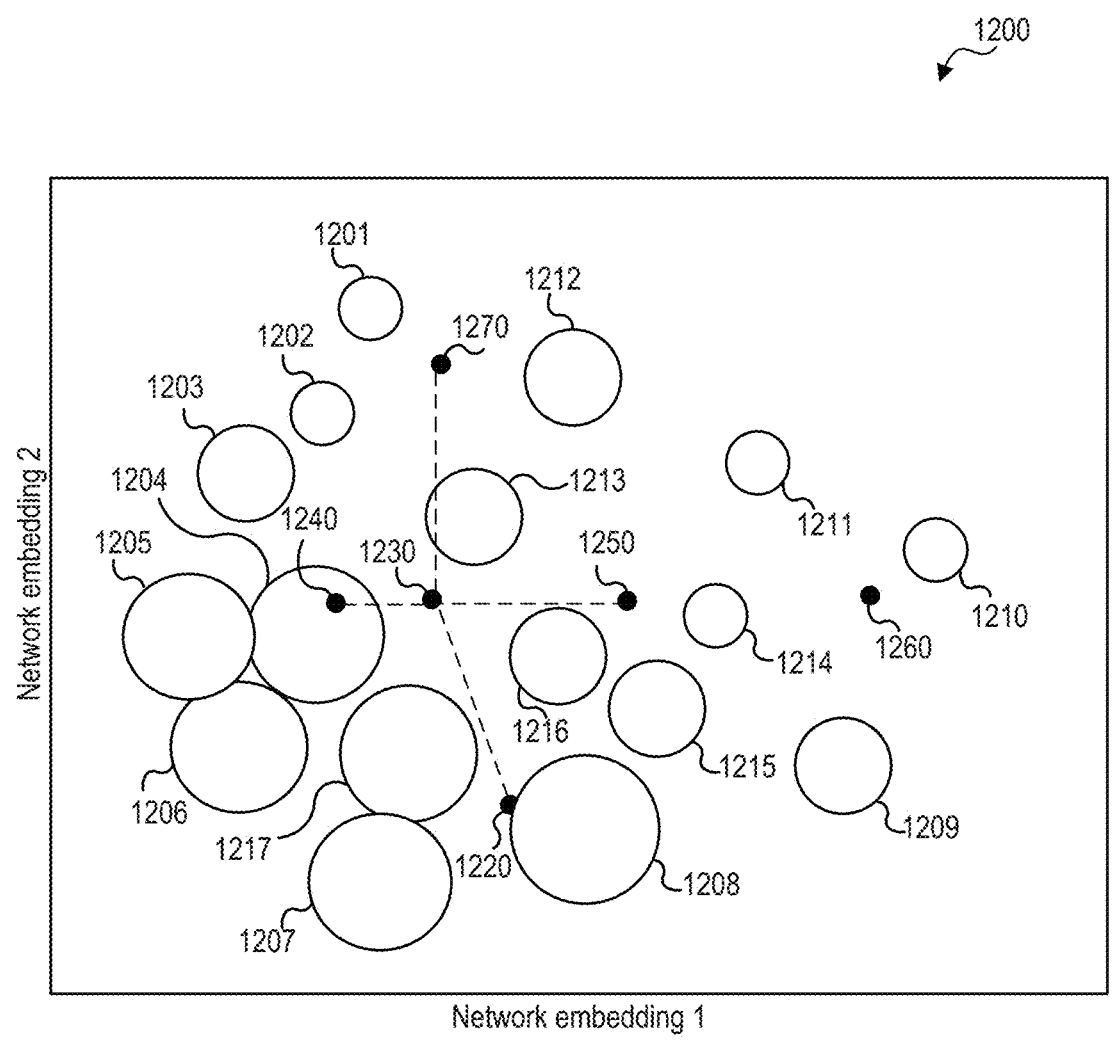
FIG. 12 shows an example output embedding for a trained and selected neural network model in conjunction with a priori ranking, according to an exemplary embodiment.
Figure 13:
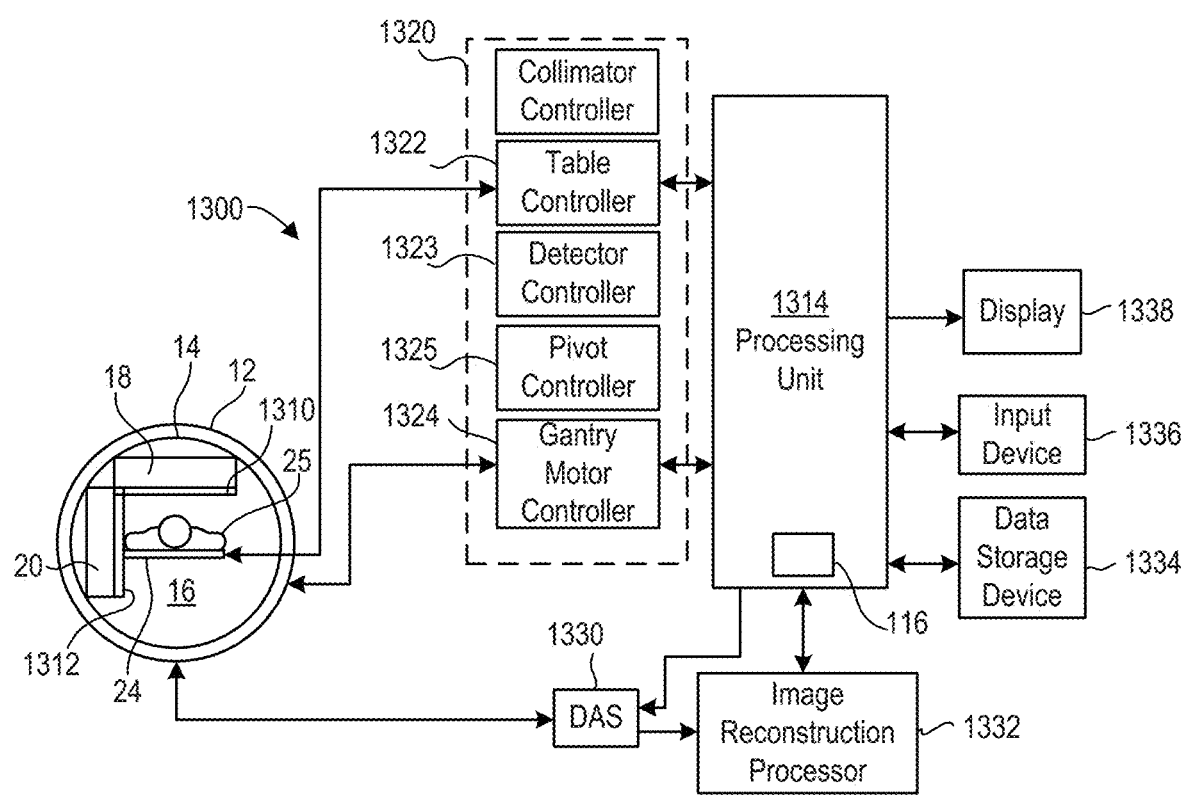
FIG. 13 is a schematic block diagram of an exemplary imaging system that may utilize an image processing system, such as image processing system of FIG. 1, and implement a computational model, such as the deep learning model of FIG. 2, for follow-up functional imaging evaluation, according to an exemplary embodiment.

The corresponding output of each of the plurality of trained models includes embeddings of the base structure and its perturbations. The output space may have a greater number of dimensions. However, for the sake of illustration, an example two dimensional output space and corresponding base structure mappings with respect to an example training set with perturbations based on the un-perturbed set shown in FIG. 7A is illustrated at FIG. 7B. Each of the trained neural network models may be inferred separately as discussed at FIG. 8, and evaluation of at least two structures with the trained neural network models is described at FIG. 9. An exemplary inference of an anatomical structure taken during a baseline imaging and a follow-up imaging is described with respect to FIG. 10. Further, in one exemplary embodiment, a relatively small number of a priori ranked (or clinically classified) lesions can be used to estimate a ranking of a new analyzed lesion, as discussed at FIG. 11. An exemplary evaluation of a new structure based on one or more a priori ranked structures is shown at FIG. 12. Further, an exemplary imaging modality that may implement the deep learning model discussed herein is shown at FIG. 13.

Referring to FIG. 1, a medical image processing system 100 is shown, in accordance with an exemplary embodiment. In some embodiments, the medical image processing system 100 is incorporated into a medical imaging system, for example, an MRI system, CT system, X-ray system, PET system, SPECT system, ultrasound system, etc. In some embodiments, the medical image processing system 100 is disposed at a device (e.g., edge device, server, etc.) communicably coupled to the medical imaging system via wired and/or wireless connections. In some embodiments, the medical image processing system 100 is disposed at a separate device (e.g., a workstation) which can receive images from the medical imaging system or from a storage device which stores the images generated by the medical imaging system. The medical image processing system 100 may comprise image processing system 31, user input device 32, and display device 33.

Image processing system 31 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration. According to other embodiments, the processor 104 may include other electronic components capable of carrying out processing functions, such as a digital signal processor, a field-programmable gate array (FPGA), or a graphic board. According to other embodiments, the processor 104 may include multiple electronic components capable of carrying out processing functions. For example, the processor 104 may include two or more electronic components selected from a list of electronic components including: a central processor, a digital signal processor, a field-programmable gate array, and a graphic board.

In still further embodiments the processor 104 may be configured as a graphical processing unit (GPU) including parallel computing architecture and parallel processing capabilities.

Non-transitory memory 106 may store deep neural network module 108, training module 110, inference module 112, and medical image data 114. Deep neural network module 108 may include at least a deep learning model comprising a plurality neural network models, and instructions for implementing the deep learning model to receive a baseline medical scan image of an anatomical structure and a follow-up medical scan image of the anatomical structure and determine one or more of a similarity, a similarity index, and a direction of change (e.g., direction of disease progression) between the baseline medical scan image and the follow-up medical scan image. For example, deep neural network module 108 may store instructions for implementing a plurality of neural network models, such as an exemplary convolutional neural network (CNN) shown at FIG. 3. Deep neural network module 108 may include trained and/or untrained neural networks and may further include various data, or metadata pertaining to the one or more neural networks stored therein.

Non-transitory memory 106 may further store training module 110, which comprises instructions for training one or more of the deep neural networks stored in deep neural network module 108. Training module 110 may include instructions that, when executed by processor 104, cause image processing system 31 to conduct one or more of the steps of method 400 for generation of plurality of training data sets, and method 600 for training the plurality of neural network models with the plurality of training data sets, discussed in more detail below. In some embodiments, training module 110 includes instructions for implementing one or more gradient descent algorithms, applying one or more loss functions, and/or training routines, for use in adjusting parameters of one or more deep neural networks of deep neural network module 108. Example protocols implemented by the training module 110 may include techniques known in the art as 'few-shot', 'single-shot', 'one-shot' or 'zero-shot' learning protocols such that that the deep learning model can be trained on a relatively small set of known examples and can classify or discriminate between new input types that were not used for the training.

Non-transitory memory 106 also stores an inference module 112 that comprises instructions for testing new data with the trained deep learning model. Further, evaluation of one or more new structures with the trained deep learning model may be performed with the inference module 112 as described at FIGS. 8 and 9. In particular, inference module 112 may include instructions that, when executed by processor 104, cause image processing system 31 to conduct one or more of the steps of methods 800 and 900, as discussed further below.

Non-transitory memory 106 further stores medical image data 114. Medical image data 114 includes for example, functional imaging images captured by a functional imaging modality, such as SPECT and PET systems, MR images captured from an MRI system, ultrasound images acquired by an ultrasound system, etc. For example, the medical image data 114 may store baseline and follow-up medical scan images. Further, the medical image data 114 may store a priori structures. In some embodiments, medical image data 114 may include a plurality of training sets generated as discussed at method 400, and further include one or more un-perturbed set of base structures that may be used for generating the plurality of training sets.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Image processing system 100 may further include user input device 32. User input device 32 may comprise one or more of a touchscreen, a keyboard, a mouse, a trackpad, a motion sensing camera, or other device configured to enable a user to interact with and manipulate data within image processing system 31. As an example, user input device 32 may enable a user to analyze and rank a priori structures as discussed at FIG. 11.

Display device 33 may include one or more display devices utilizing virtually any type of technology. In some embodiments, display device 33 may comprise a computer monitor, and may display unprocessed and processed MR images and/or parametric maps. Display device 33 may be combined with processor 104, non-transitory memory 106, and/or user input device 32 in a shared enclosure, or may be peripheral display devices and may comprise a monitor, touchscreen, projector, or other display device known in the art, which may enable a user to view medical images, and/or interact with various data stored in non-transitory memory 106.

It should be understood that image processing system 100 shown in FIG. 1 is for illustration, not for limitation. Another appropriate image processing system may include more, fewer, or different components.

FIG. 2 shows a schematic illustration of a computational model 200 including a deep learning computational model 201a (also referred to as deep learning model herein) that may be implemented for evaluation of comprehensive structural change of a structure obtained at different times. The deep learning model 201a may be implemented based on instructions stored in non-transitory memory, such as non-transitory memory 106 of the image processing system 31 at FIG. 1. In particular, during follow-up analysis using functional imaging modalities, such as SPECT and PET imaging, a baseline image of one or more of an internal anatomical structure, such as a lesion, and distribution and intensity of a physiological process may be obtained during a first medical scan. Subsequently, one or more follow-up medical scans may be performed to evaluate changes to the one or more internal anatomical structure and physiological process, for example, in response to a treatment, so as to evaluate efficacy of the therapy, disease progression, etc. The deep learning model 201a may be utilized to determine if the baseline image of the structure taken at a first time point and a second follow-up image of the structure taken at a second later time point shows structural differences, and to evaluate a degree of structural difference between the baseline image and the follow-up image.

In order to implement the deep learning model 201a for determining the structural difference and the degree of structural difference between the baseline and the follow-up images, the deep learning model 201a is constructed and trained. The trained model is then tested (the testing may be alternatively referred to as inference) with new inputs, such as the baseline and the follow-up images, and the results of the inference indicate if the baseline structure and the follow-up structure are different and a degree of structural difference.

Further, the computational model 200 includes a statistical change component 201b to evaluate a statistical value change. The statistical change component 201b may include determining a radiotracer activity difference, that is, a statistical value change of radiotracer uptake activity of the structure during the first medical scan at a first time point, and radiotracer uptake of the structure during the second medical scan at a second later time point. The statistical change component 201b may then be combined with the level of structural change determined by the deep learning model 201a to provide a comprehensive evaluation of the one or more internal anatomical structure and physiological process under evaluation.

The deep learning model 201a includes a training data set construction component 202 that includes generation of a plurality of training data sets, wherein each training data set has a different perturbation level. The construction of plurality of training data sets may be implemented by a perturbation algorithm stored in non-transitory memory, such as non-transitory memory 106 at FIG. 1, and includes constructing a first un-perturbed set of base structures 203. The first un-perturbed set of base structures may include a plurality of base structures that cover a range of relevant spatial frequencies, orientations, and different combinations that increase variability of base structures. In one example, the first un-perturbed set of base structures may include synthetic base structures derived based on known or expected lesion structural motifs, and variations of the synthetic base structures. In another example, the first un-perturbed set of base structure may include one or more regions from previously clinically known base structures. For example, the one or more regions may include common structural motifs in one or more previously known lesion structures. In yet another example, the first un-perturbed set of base structure may include a combination of synthetic structures and regions from known structures. Details of generating the first un-perturbed set of base structures will be described with respect to FIG. 4, and an example unperturbed set of base structures are illustrated at FIG. 7A.

The construction of plurality of training data sets further includes generating a plurality of training data sets with perturbations (alternatively referred to as plurality of perturbed training data sets). To generate the plurality of perturbed training data sets, each base structure in the first un-perturbed set may be perturbed multiple times to produce random variations of the base structure. Different levels of perturbations, such as first degree of perturbation, second degree of perturbation, up to $n^{th}$ degree of perturbation, may be applied to the first un-perturbed set to construct the plurality of training data sets with perturbations. For example, a first degree of perturbation may be applied to the unperturbed set of base structures 203 to generate a first perturbed training data set 204 (that is, training set with $1^{st}$ perturbation level); a second degree of perturbation may be applied to the unperturbed set of base structures 203 to generate a second perturbed training data set 206 (that is, training set with $2^{nd}$ perturbation level); and so on up to a $n^{th}$ degree of perturbation is applied to the unperturbed set of base structures 203 to generate n perturbed training data set 208 (that is, training set with $n^{th}$ perturbation level). A number of perturbed training sets may be greater than 2 (that is n is any positive integer greater than 2) and may be based on one or more of a processing capability of the processor deploying the computational model, structure physical size (e.g., smaller structures may require fewer data sets for training), spatial voxel size as determined by the imaging system output, and the desired accuracy of structure comparison (e.g., higher desired accuracy may require larger number of data sets for training).

The perturbations may span structural and image quality perturbations, and may include one or more of random linear translations (e.g., changes in position along x or y-axis within a pixel square of pixel enclosing a base structure, or changes in position along x, y, or z-axis within a box of voxel), rotations of the base structure along a random axis, resizing, and added image noise. The different levels of perturbations may be randomly selected from a distribution size which may be different for each level. Details of generating the plurality of training data sets with perturbations will be described with respect to FIG. 4, and an example illustration of the different perturbations is shown at FIG. 5. In this way, by generating a plurality of training data sets with different perturbation levels, the training process need not depend on collection of large clinical data.

The deep learning model 201a further includes a training component 209, wherein upon generating the plurality of training data sets with different perturbation levels, each of the plurality of training data sets is used for training each of a plurality of neural network models. As shown at 209, the first perturbed training data set 204 (having first degree perturbations) is used to train a first neural network model 210, the second perturbed training data set 206 (having second degree perturbations) is used to train a second neural network model 212, and so on up to the $n^{th}$ perturbed training data set 208 is used to train a $n^{th}$ neural network model 214. Thus, a number of neural network models may be based on a number of plurality of training data sets. In this way up to n number of neural network models may be trained, each with a different base structure data set.

Further, each of the plurality of neural network models may be configured with the same network architecture while each network model is trained with a training set having a different perturbation level. Example network architectures for building the plurality of neural network models may be based on a convolutional neural network based architecture such as siamese network, triplet network, matching network, relation network and prototypical network architectures. An example siamese network model is described below at FIG. 3.

Further, the training of each neural network model may be performed by utilizing a deep learning protocol that allows a neural network model to be trained on a relatively small set of known examples, and can classify and discriminate between new input types that were not used for training. Example deep learning protocols that may be used for training include few-shot learning, one-shot learning, and zero-shot learning.

In this way, each of plurality of neural network models having the same architecture, may be trained on a base structure data set with a different perturbation level to obtain corresponding outputs. The outputs from each neural network model may include embeddings (alternatively referred to herein as encodings) for the corresponding input base structure data set used for training. For example, a first output of the first neural network model 210 may include a first set of embeddings of base structures with first degree perturbations from the first perturbed training data set 204. In a first base structure mapping 216, the first set of embeddings may be mapped on to a first output space of the first neural network model 210, where perturbations of the same base structure are grouped together in a distribution with distribution width or standard deviation corresponding to the degree of perturbation applied to the base structure data set. Similarly, in a second base structure mapping 218, a second output of the second neural network model 212 includes a second set of embeddings of base structures with second degree perturbations from the second perturbed training data set 206, which are mapped on to a second output space of the second neural network model 212 and so on up to a $n^{th}$ output, where the $n^{th}$ base structure mapping 220 of the $n^{th}$ neural network model 214 includes a $n^{th}$ set of embeddings of base structures with $n^{th}$ degree perturbations from the $n^{th}$ perturbed training data set 208, which are mapped on to a $n^{th}$ output space 220 of the $n^{th}$ neural network model 214. In this way, each of the plurality of training data sets used as inputs into each of the plurality of network models for training may be mapped on to the corresponding output space as embeddings, where an average standard deviation of the base structure mapping is based on a level of perturbation applied to the base structures used for training. Details of training the plurality of neural network models are described with respect to FIG. 8, and example embedding maps in two-dimensional output spaces are illustrated with respect to FIGS. 7B, 10, and 11.

Next, upon training, each of the plurality of trained models may be used in inference 236 for testing or validation of new inputs. In this example, a first input 230, which is a baseline image of a structure, which is a lesion structure in this example, taken at a first earlier time point, and a second input 232, which is a follow-up image of the same lesion structure of the baseline image taken at a second later time point, are used for inference. The first input 230 includes a baseline structure image 231, and the second input 232 includes a follow-up structure image 233. Although the images 231 and 233 are of the same structure, it may be noted that the lesion structure has undergone a structural change between the first and the second time points. While the present example shows the input structure as a lesion, it will be appreciated that evaluation of other structures, such as cysts, sarcomas, polyps, nodules, glands, tumors, metastasizes, plaques, patches of fine-texture tissues, etc., with the deep learning model 201a, are also within the scope of the disclosure.

Prior to inference at 236, the structure images 331 and 333 may be analyzed by value normalization at 234. Value normalization may include, for each image, normalizing the image values to a robust maximum of the whole structure value distribution (the robust maximum may be a mean or median of the highest 5% of the voxels, for example). The first and second pre-normalized or normalized image values for the first and second structure images 231 and 233 may be further used for a subsequent statistical value comparison at 244.

Returning to 236, the inference may be performed for each model separately. During inference, each of the plurality of trained neural network models may receive the baseline structure image 231 and the follow-up structure image 232 as inputs. For example, baseline image 231 and follow-up image 232 are entered as inputs into each of first trained neural network model, second trained neural network model, and so on up to $n^{th}$ trained neural network model. As shown, the image values may be normalized prior to inputting in to each model.

Each trained model may output embeddings of the baseline structure image 231 and the follow-up structure image 233 mapped in its corresponding output space. Said another way, the first output space of the first neural network model includes mapping of the baseline structure image 231 and the follow-up structure image 333. Thus, a first mapping 238 of the input structures 231 and 233 as embeddings in the first output space of the first trained neural network model is generated. Similarly, a second mapping 240 of the input structures 231 and 233 as embeddings in the second output space of the second trained neural network model is generated and so on until $n^{th}$ mapping 242 of the baseline structure 231 and the follow-up structure 233 in the $n^{th}$ output space of $n^{th}$ trained model is generated. In this way, each of the trained models outputs embeddings of the baseline structure image 231 and the follow-up structure image 233 mapped in its corresponding output space. Thus, each trained neural network model is inferred separately with the same set of inputs comprising the baseline structure image 231 and the follow-up structure image 233, and as such, n number of mappings of the same set of inputs are generated.

Next, the deep learning model 201a includes an evaluation 246, where the input structure mappings are evaluated with respect to base structure mappings in the respective output space. Specifically, the evaluation 246 of the input structure mappings may be based on a distance between the mapped embeddings of the two input structures (baseline 231 and follow-up 233) in each output space, and on a statistical distribution width of one or more base structure mappings grouped together in the vicinity of the input structure embeddings in each output space. Thus, each of the first to $n^{th}$ mapping of the baseline structure 231 and the follow-up structure 233 may be evaluated in the respective first to $n^{th}$ output space with respect to the corresponding mappings of the base structure embeddings. Following the evaluation, the deep learning model may include a structural change determination component 248, wherein a level of structural change may be determined based on the evaluation. In one exemplary embodiment, a standardized similarity score based on a comparison of the baseline and follow-up images of a lesion may be generated, wherein the similarity score is standardized based on a degree of perturbation of a plurality of base structures that corresponds to the change between the baseline and follow-up images.

Figure 8:
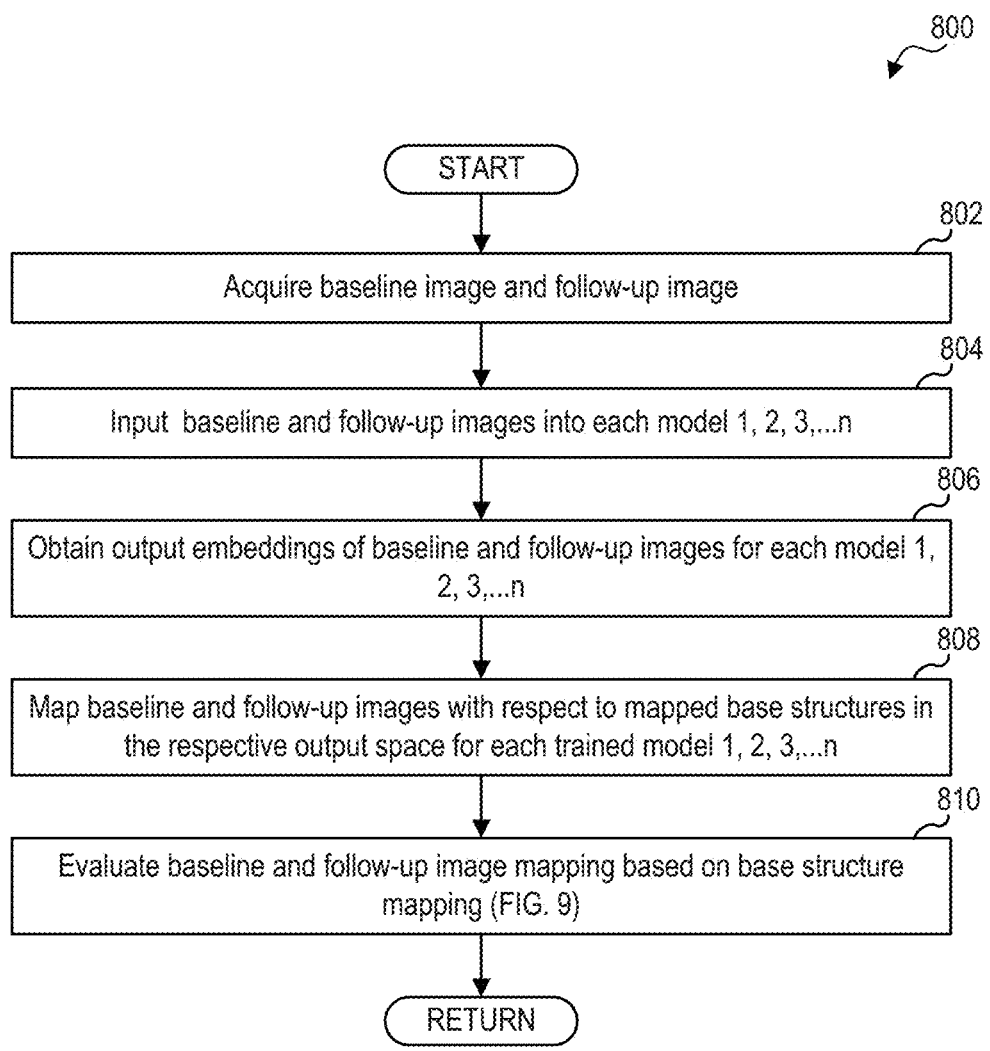
FIG. 8 is a high-level flow chart illustrating a method for inference with a plurality of trained neural network models, according to an exemplary embodiment.
Figure 9:
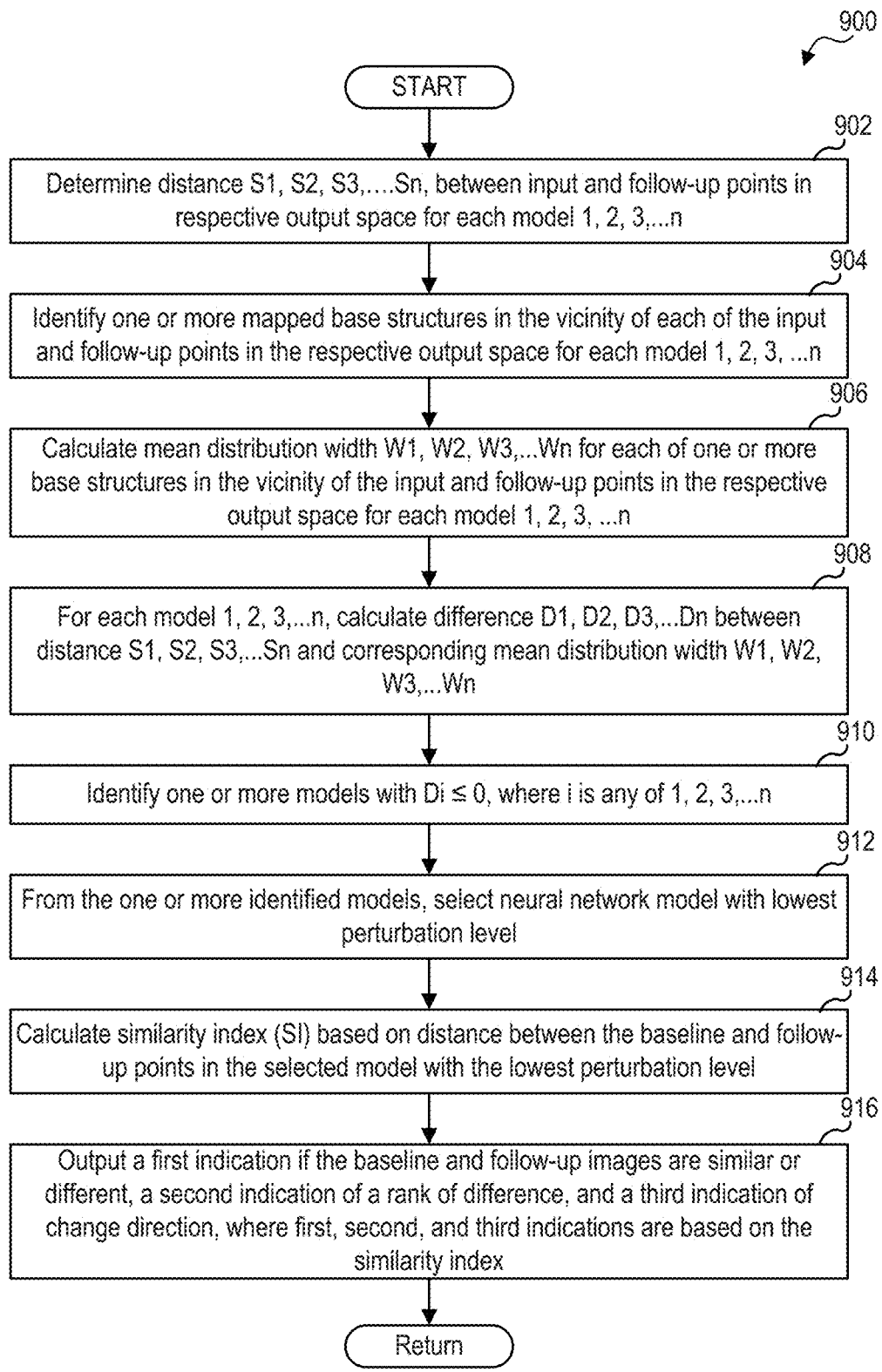
FIG. 9 is a high-level flow chart illustrating a method for determining similarity between an input structure and a follow-up structure utilizing plurality of trained neural network models, according to an exemplary embodiment.

Details of evaluating the input structure mappings in each output space of each trained model with respect to the corresponding base structure mappings, and the determination of difference and a level of difference between the two input structures will be further elaborated with respect to FIGS. 8, 9, and 10.

Further, as indicated at 250, a combined structure comparison may be performed. The combined structure comparison may be based on statistical value comparison (at 244) of the statistical value change portion 201b of the computational model 200 and the structural change determination portion 248 of the deep learning model portion 201a of the computational model 200. In one exemplary embodiment, each of the statistical value comparison 244 and level of structural change 248 may be assigned different weights. Thus, a rank of similarity between the baseline structure 231 and the follow-up structure 233 may be based on a weighted average of a statistical value change and a structural change value. It may be noted that since the mapping arrangement of the trained model may be highly non-linear, an absolute distance (length) between the two points of the mapped lesions is not by itself a sufficient indication for the structural difference level. Thus, a neural network model may be selected, which has a degree of perturbation corresponding to the structural change between the baseline and the follow-up images. Thus, the structural change value may be a similarity index (also referred to herein as similarity score) based on a serial number (or degree of perturbation) of a selected neural network model trained with lowest perturbation level in a series of selected trained models. In this way, the similarity index is standardized based on a degree of perturbation of a plurality of base structures where the degree of perturbation corresponds to the change between the baseline and follow-up images.

The details of determining the similarity index will be further discussed with respect to FIGS. 9 and 10. Further, it will be appreciated that the way of combining between the two paths of analyses, the level of structural change between two input structures and the statistical value comparison, may further depend on the specific disease or conditions and based on other medical knowledge. For example, in some cancer types a lesion structures may have higher importance and weight in the medical assessment. Consequently, the structural change value may be given higher weightage than the statistical change value. While in other types, a difference in the average SUV (standard uptake value) of the tracked structure may have higher weight. As a result, the statistical value change may be given higher weightage than the structural change value. The SUV may be determined based on ratio of the image-derived radioactivity concentration and a whole-body concentration of an injected radio-isotope during functional imaging scan.

Further, it may be noted that the lesion structure alone can be analyzed after normalizing the image values to the robust maximum of the whole lesion value distribution (the robust maximum can be e.g. the mean or median of the highest 5% of the voxels).

In this way, a deep learning model comprising a plurality of neural network models, each trained with a training data set having a different perturbation level, may be implemented to evaluate a structural change of the one or more anatomical structure or physiological process tracked via functional imaging modalities. By implementing the deep learning model discussed herein structural change of tracked structures may be efficiently and more accurately evaluated and quantified without classifying them into known classes. As will be further discussed below, the deep learning model may determine a level of structural change of a concerned structure and/or physiological process over time. Utilizing the level of structural change, a directionality of disease progression or physiological profile change over time may be determined, which may be then used to prescribe appropriate treatment for a patient under observation. Furthermore, with the deep learning model, structural changes including level of structural changes to new structures and/or processes that were not used for training can be determined. As a result, efficiency and accuracy of diagnosis and evaluation with the imaging modality is improved.

Figure 3:
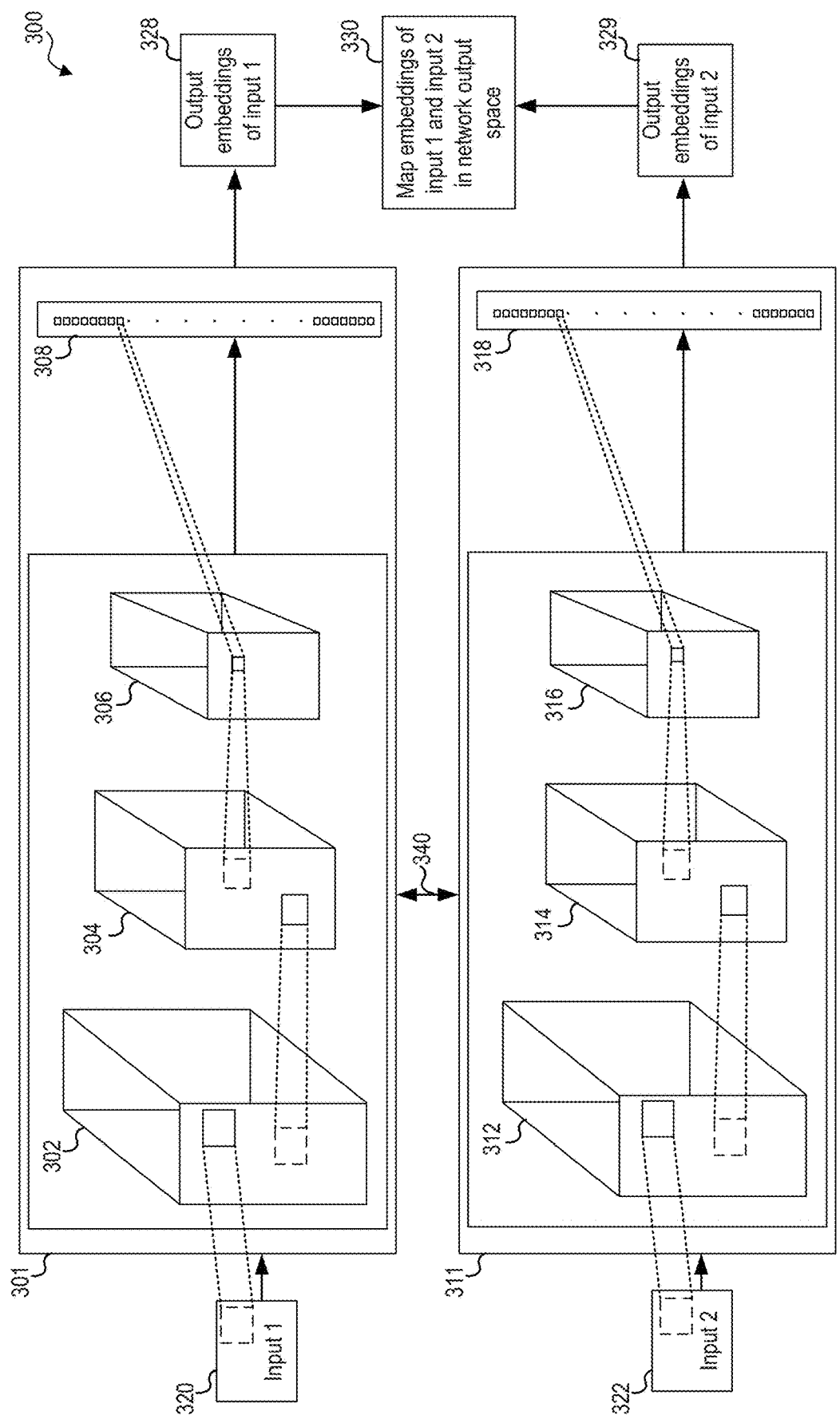
FIG. 3 is a schematic diagram illustrating an exemplary high-level neural network architecture that may be implemented with the deep learning model of FIG. 2, according to an exemplary embodiment.

Turning to FIG. 3, a high level neural network 300 that may be included in a deep learning computational model, such as the deep learning computational model 201a described at FIG. 2 above, is shown. The architecture of the neural network 300 may be implemented for all the neural network models used for learning base structure similarities in a training process, during inference of the trained models, and during evaluation for discriminating between two or more input images, according to an exemplary embodiment. For example, the deep learning model may include a plurality of neural network models. Each of the plurality of neural network models may be constructed with the same architecture, such as a siamese architecture of the neural network 300.

While the present example illustrates a siamese network architecture, other similar or derived architectures, such as a triplet network, matching network, relation network, or prototypical network, may be implemented with the deep learning computational model discussed herein for learning base structure similarities, inference, and evaluation. In particular, any network model that can be trained with small set of known examples and can be trained to differentiate between new input structures (e.g., lesions) that were not used for training may be used.

The neural network 300 includes at least two machine learning subnets, a first subnet 301 and a second subnet 311 configured as a siamese network. The first subnet 301 may be a convolutional neural network (CNN) having a sequence of convolution and pooling layers, including a first layer 302, a second layer 304, and a third layer 306. The first layer 302 is a convolutional layer, and a convolutional filter or window is depicted by a dashed rectangle. Although pooling maybe applied to an output of the convolution, subsequent layers 304 and 306 are depicted as convolutional and pooling layers, for sake of brevity. When configured as a siamese network, second subnet 311 is identical to the first subnet 301, and includes a second identical sequence of convolution and pooling layers 312, 314, and 316, where each layer 312, 314, and 316 is identical to 302, 304, and 306 respectively.

Each of the first subnet 301 and the second subnet 311 receives a first input data 320 and a second input data 322. During training of each of the plurality of neural network models of the deep learning model, the first input data 320 fed into the first subnet 301 may include a perturbed base structure sample, and the second input data 322 may include another perturbed base structure sample related to either the same structure type or a different structure type. As an example, for a neural network model with a desired degree of perturbation, the first input may include a first training structure sample related to a random perturbation with the desired degree of a randomly selected base structure type, and the second input may include a second training structure sample related to a different random perturbation (of the same desired degree of perturbation) of the same selected base structure type. In this instance, a loss function of the trained model will be based on the provided information that the two inputs are of the same type. In another example, the first input may include the first training structure sample related to the random perturbation with the desired degree of the randomly selected base structure type, and the second input may include a third training structure sample related to the random perturbation (of the same desired degree perturbation) of a different selected base structure type. In this instance, the loss function of the trained model will be based on the provided information that the two inputs are of different types. An example unperturbed base structure data set is shown at FIG. 7A, and an example perturbed base structure data set is shown at FIG. 5.

During inference of the trained deep learning model, pairs of internal structure images, may be used as input. For example, during inference of the trained deep learning model for structural comparison, the first input data 320 may include a first region including of a first medical scan image including an internal structure image (e.g., a baseline image of a lesion, the base line image taken during a first medical scan), and the second input data 322 may include a second region of a second medical scan image (e.g., a follow-up image of the lesion, the follow-up image taken during a second subsequent medical scan). It will be appreciated that a medical scan image may be a sub-volume of an image volume, and during the inference, the medical scan image can be divided into several or many smaller sub-volumes where each is inferred separately.

Turning to the first subnet 301, following each convolutional layer 302, 304, and 306, an activation layer may be included, where an activation function such as a rectified linear unit (ReLU) function, may be applied. Optionally, other activation functions, such as sigmoid functions, for achieving non-linearity may be used. Further, after applying an activation layer, in some examples, a pooling layer may be applied. An example pooling approach is a maxpooling approach, wherein a pooling filter is applied to the input volume, which then outputs a maximum number in every subregion of the input volume that the pooling filter is applied to. The pooling layer may be applied after one or more convolutional layers. In the present example, the pooling approach is applied to each layer 302, 304, and 306 in the first subnet 301. While the present example shows three convolutional and pooling layers, it will be appreciated that any number additional convolutional layers may be included. Further, any combination of convolutional and pooling layers for the first subnet 301 are also within the scope of the disclosure. Since the neural network 300 is configured as a siamese network, the configuration of the second subnet 311 is identical to the configuration of the first subnet 301. Further, as indicated by double-ended arrow 340, the first subnet 301 and the second subnet 311 of the siamese network, may share the same parameters (e.g., weights, convolution filter parameters, pooling filter parameters, activation function parameters, hidden layer parameters etc.). Example models where one or more parameters change between the first and the second subnets, for example based on differences in the two input data sets, are also within the scope of the disclosure.

Following the last layer in the first and second subnets 301 and 311, are first fully connected layer 308 and second fully connected layer 318, respectively. The fully connected layers 308 and 318 may take as inputs, a respective output of a preceding layer. In the present example, the preceding layer for the first fully connected layer 308 is the third convolution and pooling layer 306, however the preceding layer can be any preceding layer, such as a convolution layer, a ReLU layer, or a pooling layer. All example functions and operators described herein may be implemented to work with either 2D or 3D input data structures as in medical imaging.

An output of the fully connected layer 308 is a "d" dimensional vector, where "d" is based on optimization that balances between high capability of training structure differentiation to minimizing non-linearity which enables the task of new structure differentiation. For example, if "d" is equal to the number of base structures, this may give high classification capabilities of structures from similar types of the trained base structures, but may not be very useful for discriminating new different structures due to the highly non-linearity of the mapping to the embedding space. As such, for few-shot learning, the output vector dimension may be selected to be about one or two orders of magnitude smaller than the number of training base structures. For example, in the example of FIG. 7A of 61 base structures, dimension "d" may be between 2 to 6. Thus, the output of fully connected layer 308 includes "d" dimensional encoding of the input image, where the number of dimensions "d" is less than the number of training base structures. As a result, the first subnet 301 outputs encodings 328 of the first input data 320 and the second subnet 311 outputs encodings 329 of the second input data 322. While the present example shows a single fully connected layer, one or more additional fully connected layers are within the scope of the disclosure. Further, in some examples, the fully connected layer may not be used, in which case the network 300 may be a fully convolutional siamese network. Thus, different network configurations with or without the fully connected layer(s) are possible. Furthermore, variations of siamese network architecture, including hidden layers, that may be implemented with few-shot, one-shot, zero-shot, or other learning protocols that allow classification or discrimination between new input types that were not used for the training, are also within the scope of the disclosure.

The encodings 328 and 329 may then be mapped in a network output space of the neural network 300, as depicted at 330. As discussed above, the output space may include "d" dimensions, based on the output encodings. It may be noted that the encodings are high-dimensional, and thus, in some examples, in order to facilitate one or more of visualization and inference, the high-dimensional output space of the selected neural network model may be transformed into a two or three dimensional Euclidean space by implementing a dimension reduction technique, such as principal component analysis (PCA) or T-distributed Stochastic Neighbor Embedding (t-SNE). Example output space with synthetic base structures mapped in two dimensions is shown at FIG. 7B, FIG. 10, and FIG. 12

Figure 4:
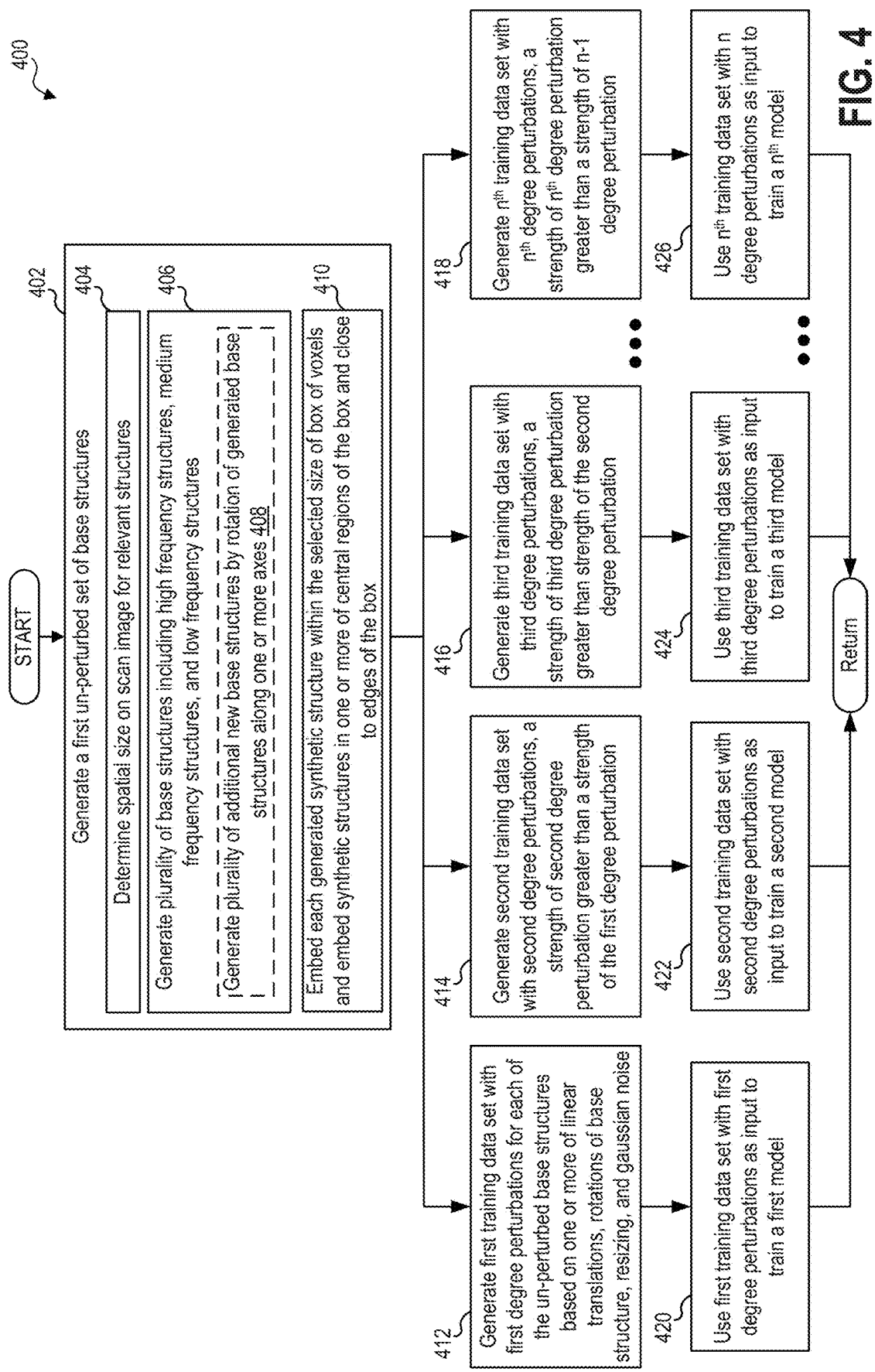
FIG. 4 is a high-level flowchart illustrating a method for generating plurality of base structure data sets, according to an exemplary embodiment.
Figure 5:
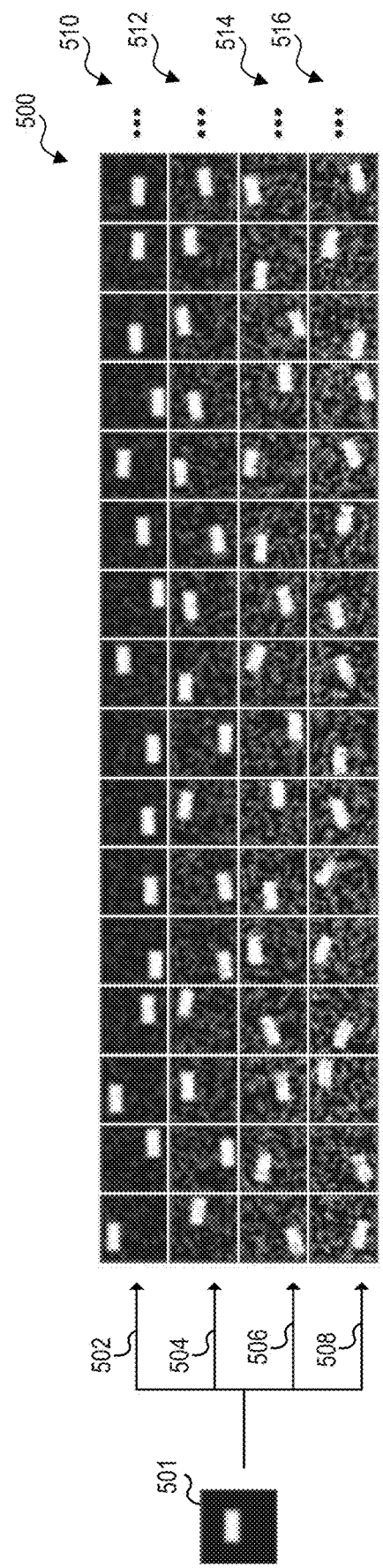
FIG. 5 is a schematic diagram illustrating plurality of perturbations applied to a base structure, according to an exemplary embodiment.

Next, FIG. 4 is a high-level flow chart illustrating a method 400 for generating a plurality of training data sets for training a deep learning model, such as deep learning model 201a at FIG. 2. The deep learning model includes a plurality of neural network models, such as first neural network model, second neural network model . . . $n^{th}$ neural network model discussed at FIG. 2. Each of the plurality of training data sets may be utilized for training each of the plurality of neural network models for learning structural similarity among the various structures in the plurality of training data sets and evaluating whether an analyzed structure (or a region) in a medical scan image has structurally changed and the extent of structural change between at least two evaluation studies (baseline and follow-up) during functional imaging analysis, as further discussed below. Method 400 may be implemented by a perturbation algorithm stored in non-transitory memory, such as non-transitory memory 106 of the medical image processing system 100, an edge device connected to the image processing system, a cloud in communication with the image processing system, or any appropriate combination thereof.

Method 400 begins at 402, which includes generating a first un-perturbed set of base structures. The first un-perturbed set of base structures is the set of base structures before any perturbation or random variation are applied. An example un-perturbed set of base structures is shown and further described at FIG. 7A. The un-perturbed set of base structures may form a foundation for subsequent plurality of training base structure generations.

Generating the first un-perturbed set of base structures includes, at 404, determining a spatial size on scan images in which relevant structures are embedded. Specifically, in order to construct a set of training base structures, the spatial size of a box of voxels in which relevant structures are embedded may be determined. The spatial size may be based on a spatial size range for the relevant structures. The relevant structures may include one or more of lesions and abnormalities in anatomical structures. The spatial range on scan images may be based on one or more of type of lesion (e.g., location in the body, lesion class such as bone lesion, soft tissue etc.), a type of diagnostic purpose and the corresponding diagnostic method (e.g., functional imaging), physical characteristics of relevant lesions (e.g., size), a type of imaging system used (e.g., SPECT versus MM), and image output parameters of the corresponding system (e.g., resolution). For example, in functional molecular imaging, the spatial range on the images of relevant lesions for diagnostics purpose can be typically varied between very few image voxels in each spatial dimension to about 30 image voxels in each spatial dimension. This depends on the lesion physical size and the spatial voxel size as determined by the imaging system output. Thus, for functional molecular imaging modalities, a box of $14^3$ or $28^3$ voxels may be selected. While the above example illustrates selecting a box of $14^3$ or $28^3$, it will be appreciated that the selection of spatial size may be based on one or more parameters for determining spatial size as discussed above, including a type of lesion, one or more lesion characteristics, the corresponding diagnostic purpose, and imaging system parameters.

Generating the first un-perturbed set of base structures further includes, at 406, generating a plurality of base structures, including high spatial frequency structures (alternatively referred to as high frequency structures), medium spatial frequency structures (alternatively referred to as medium frequency structures), and low spatial frequency structures (alternatively referred to as low frequency structures). The plurality of base structures in the first un-perturbed set of base structures may include one or more of synthetic base structures, structural motifs from known lesion structures, and expected lesion structures. In one example, the one or more synthetic base structures may be derived from known lesion structures. The known lesion structures may include one or more of common motifs in lesions and unique lesion structures that are unique to a particular disease. In another example, the structural motifs from known lesion structures may include common motifs in lesions.

The synthetic base structures comprise a range of relevant spatial frequencies, orientations, and different combinations of spatial frequencies and orientations. Specifically, the synthetic base structures may include one or more of high frequency structures medium frequency structures, and low frequency structures generated from one or more subsets of voxel sizes within the selected box of voxels. High frequency structures may be generated from a first subset of box of voxels, medium frequency structures may be generated from a second subset of box of voxels, and low frequency structures may be generated from a third subset of box of voxels, where the first subset of box of voxels is smaller in size than the second subset, which is smaller than the third subset. Further, a number of boxes in the first subset may be greater than or equal to a number of boxes in the second subset, which may be greater than or equal to a number of boxes in the third subset. For example, if a box of $14^3$ voxels is selected, high frequency structures may be generated from combinations of two, three, or four small boxes of $2^3$ voxels in different arrangements. Medium frequency structures may be generated from combinations of two medium boxes of $3^3$ voxels. Low frequency structures may be generated from single boxes of lengths in the range of 4-6 voxels (in each dimension). Further, different arbitrary combinations of one or more of high, medium, and low frequency structures may be generated. Further, it will be appreciated that the range of frequencies may be based on a size of box of voxels selected. As the size of the selected box of voxels increases, a greater spatial frequency range of structures may be generated in addition to high, medium, and low frequencies discussed above.

Further, optionally, at 406, rotated configurations of the generated structures, for example 90 degrees, along one or more axes, may be included as new different structures.

Furthermore, generating the first un-perturbed set of base structures includes at 410, embedding each generated synthetic structure within the selected size of box of voxels, and further includes, embedding the synthetic generated structures in one or more of the central regions of a selected box size of the box of voxels, and close or attached to the edges of the box of voxels. Overall, various combinations of different frequencies and rotations may increase the variability of the base structures. An example un-perturbed set of base structures, each embedded within a selected box of voxels is illustrated at FIG. 7A. FIG. 7A also illustrates synthetic structures within one or more central regions of the total box size, and edge structures that are positioned close to or attached to the edges of the total box.

Upon generating the first un-perturbed set of base structures, method 400 proceeds to generate plurality of training data sets each with varying levels of perturbations, as indicated at 412, 414, 416, and 418. In order to train a neural network model via a learning protocol, such few-shot learning, plurality of training data sets with random variations of the first set of un-perturbed base structures may be generated. The random variations will be considered during the training process as belonging (identical) to the same type of their un-perturbed structure. The plurality of training data sets may be generated in parallel as indicated at 412, 414, 416, and 418. Alternatively, the plurality of training data sets may be generated sequentially, depending on the capabilities of the processor executing the generation commands.

At 412, method 400 includes generating a first training data set by applying first degree perturbations to each un-perturbed base structure in the first un-perturbed set of base structures. That is, the first training data set having the first degree of perturbation may be generated from the first un-perturbed set. The first degree of perturbations may be based on one or more of structural variations and image quality variations. Specifically, the first degree of perturbations may include, for each un-perturbed base structure, one or more of a linear translation of the base structure along a random axis within its voxel box, a rotation of the base structure, a resizing of the base structure, and an added image noise. The perturbations may be applied separately, in any combination, or altogether. In addition, other morphological perturbation types can be applied such as skewing or stretching in one direction (e.g. while keeping structure attached to an edge of the box). In an exemplary embodiment, the first training data set may include a desired number of perturbations for each un-perturbed base structure, where the desired number of perturbations is based on a size of voxel box selected, and/or the desired accuracy of structure comparison.

At 414, method 400 includes generating a second training data set by applying second degree perturbations to each un-perturbed base structure in the first un-perturbed set of base structures. The second degree perturbations has a strength or level of randomness different from the first degree perturbations. The strength or level of randomness may be based on a standard deviation of a corresponding distribution for each perturbation type. Thus, the degree of perturbation may be adjusted by controlling a standard deviation of the corresponding distribution for each perturbation type (e.g., linear translation, rotation, resizing, and image noise).

In one exemplary embodiment, assuming the first training data set has a lowest level (or lowest degree) of perturbations, the second training data set may have a higher degree of perturbation with respect to the first training data set. Thus, the second degree of perturbations may be greater strength or have a higher level of randomness compared to the first degree of perturbations. As an example, for a first distribution of linear translations along a random axis, a standard deviation of the first distribution for the second degree of perturbations may be greater than the standard deviation of the first distribution for first degree of perturbations. Similarly, for a second distribution of small rotations along a random axis, a standard deviation of the second distribution for the second degree of perturbations may be greater than a standard deviation of the first degree of perturbations. Also, for a third distribution of resized base structures, a standard deviation of the third distribution for the second degree of perturbations may be greater than the standard deviation of the third distribution for first degree of perturbations. Similarly, for image noise type perturbations, for a fourth distribution of base structures having added image noise, a standard deviation of the fourth distribution for the second degree of perturbations may be greater than the standard deviation of the fourth distribution for the first degree of perturbations.

In another exemplary embodiment, the second training data set may have a lower degree of perturbation with respect to the first training data set. Thus, in this example, the second degree of perturbations may be of lower strength or have a lower level of randomness compared to the first degree of perturbations.

At 416, method 400 includes generating a third training data set by applying a third degree of perturbation to each un-perturbed base structure in the first un-perturbed set of base structures. The third degree of perturbation may be different from each of the first and the second degree perturbations. Thus, the third training data set has a third degree of perturbation different from the first and second degree perturbations applied to the first and second training data sets respectively.

In one example, the third training data set may have a higher degree of perturbation with respect to the second training data set. Thus, the third degree of perturbations may have a greater strength or have a higher level of randomness compared to the second degree of perturbations. As a result, a standard deviation of a corresponding distribution for each perturbation type (e.g., linear translation, rotation, resizing, and image noise) is greater for the third degree perturbations compared to the second degree perturbations. Examples where the third degree of perturbation of the third training data set is lower than one or more of the first and second degree perturbations are also within the scope of the disclosure.

Similar to the first, second, and third training data sets discussed at 412, 414, and 416, as a plurality of training data sets may be generated. Thus, at 418, an $n^{th}$ training data set having an $n^{th}$ degree perturbation may be generated, where a strength of the $n^{th}$ degree perturbation is different from each of the (n−1) degree perturbations (that is, any of the perturbation levels of any previous training data set).

In one example, a strength of the $n^{th}$ degree perturbation may be greater than the (n−1) degree perturbation (that is an immediate previous perturbation of an immediate previous training data set). Examples where the $n^{th}$ degree of perturbation of the $n^{th}$ training data set is lower than one or more of the first, second, third, and so on up to (n−1) degree perturbations are also within the scope of the disclosure.

In this way, each training data set has a different perturbation level for different control parameters. Thus, a training set with the highest degree of perturbation has a wider distribution (due to having the greatest standard deviation). Further, as discussed above, a training set may include perturbations of more than one control parameter, in which case, an average standard deviation of the one or more standard deviations for each of the control parameters may be considered. In any case, an average standard deviation is different for each of the plurality of training data sets.

While the present example illustrates the second degree perturbations applied to each un-perturbed base structure in the first un-perturbed set of base structures, it will be appreciated that embodiments where the subsequent training sets are generated from previous training data sets by changing the perturbation level are also within the scope of the disclosure. That is, embodiments where subsequent data sets are generated sequentially, where the subsequent degree perturbations (second, third, fourth, etc.) are applied to each base structure in the previous training data (first, second, third, etc.) set to generate subsequent training data sets (second, third, fourth, etc.) are also within the scope of the disclosure.

In this way, during the generation of n training data sets, the effectiveness (the level/degree) of random perturbations is changed (for example, from low level to high level). Thus, each training data set has a different perturbation strength. Further, one or more control parameters may control the level of random perturbations. The one or more control parameters include the standard deviation of a first distribution of linear base structure translation along a random axis, the standard deviation of second angular distribution of small rotations along a random axis, and the standard deviation of a third distribution of the resizing factor (e.g. between 0.9 to 1.1). The one or more control parameters may be changed between the several different trained models, while using the same computational process of generating the random perturbations.

Further, different control parameters may be changed between different training sets while keeping at least one control parameter same among the different sets. However, in general, all control parameters may be changed between different training sets. For example, consider a first subset of four training data sets of the plurality of training data sets, the first subset comprising the first training data set, the second training data set, the third training data set, and the fourth training data set. The first training set may include perturbations that are linear translations, the second training set may include perturbations that are rotations along a random axis, the third training set may include perturbations that are based on resizing of the base structures, and the fourth training set may include perturbations that include added image noise. Thus, each training data set in the first subset has variation in one control parameter. In the above example, the first training set includes perturbations that are variations in linear translations of the base structures within the voxel box, and the distribution of linear translations has a first standard deviation (SD). The second training set includes perturbations that are variations in the rotation of the base structures along random axes, and the distribution of the random rotations has a second SD. The third training set includes perturbations where the base structures are resized based on one or more resizing factors, and the distribution of resized base structures in the third training data set has a third SD. The fourth training set has variations of image noise (e.g., a range of added image noise) that are added to the base structures, and the distribution of image noise variations has a fourth SD. In this example, each of the first, second, third, and fourth standard deviations may have different values. As a non-limiting example, fourth SD>third SD>second SD>first SD.

In some examples, each training set may include perturbations in more than one control parameter. For example, at least one control parameter (e.g., linear translation, rotation, resizing, and image noise) may be maintained as consistent (or within a threshold same standard deviation) among the different subsets of training sets while perturbation levels of one or more other control parameters are changed among the different training sets. Thus, an average standard deviation (also referred to herein as mean SD) of a training data set is different for each training data set. In other words, each training data set has a different average standard deviation. For example, the first training data set may have a set variation in linear translation and one or more additional variations in rotation, resizing, and image noise. As such, for the first training data set, the distributions of linear translations, rotations, resizing, and image noise may have a first average standard deviation, where the first average standard deviation based on distributions of linear translations, rotations, resizing, and added image noise. The second training data set may have the set variation in linear translation while a degree of the one or more additional variations in rotation, resizing, and image noise may be changed such that it is different from a degree of one or more additional variations in the first data set. Thus, the second training data set may have a second average distribution that is different from the first training data set. For example, if the degree of the additional variations are increased, an average SD of the variations in the second training data set may be greater than the average SD of the variations in the first training data set; and if the degree of additional variations are decreased, the average SD of the variations in the second training data set is greater than the SD of the variations in the first training data set. Similarly, the third and the fourth training data sets may have different variations in the additional control parameters (e.g., rotation, resizing, and image noise) while the first set variation of the linear translation may be maintained the same such that an average SD of the variations in the third data set and an average SD of the variations in the fourth data are not the same. Thus, the average SD of each of the first, second, third, and fourth variations is different. In this way, each training set has a different SD of variation applied to it, and thus sufficient number of variations of the same base structure may be generated for training.

While the above example is illustrated by maintaining the amount of linear translation as constant between the different data sets, any control parameter may be selected to be maintained as constant. Further, for different subsets, different control parameters may be selected to be maintained as constant.

By generating and implementing neural network model training with plurality of data sets, as discussed herein, the need for large clinical data for model training can be significantly reduced. Further, by utilizing the plurality of training data sets with different perturbation levels, the need to label or to give in advance specific ranks to the different base structures can be significantly reduced, and furthermore, the generation of plurality of training data sets with different perturbation levels via the computational process does not require manual selection and designing of specific lesion features. As a result, annotation workload is significantly reduced while efficiency detecting similarity or differences are improved as the method can generate sufficient variation in the datasets.

An example of four training data sets with different perturbation parameters and different perturbation levels is shown at FIG. 5.

Turning to FIG. 5, an example set 500 of four training data sets generated from an example base structure is illustrated. Specifically, one base structure 501 is shown, and four data sets generated from the base structure, a first data set 510, a second data set 512, a third data set 514, and a fourth data set 516, each with a different degree of perturbation, are shown. Each of the data sets 510, 512, 514 and 516 will be used for training four neural network models. The base structure 501 is shown as a 2-dimensional base structure for illustration purposes. It will be appreciated that 3-dimensional base structures may be perturbed in a similar manner. Each data set 510, 512, 514, and 516 may be generated by a computational process (e.g., perturbation algorithm) executed by a processor, such as processor 104 of the image processing system 31 described at FIG. 1, an edge device connected to the image processing system, a cloud in communication with the image processing system, or any appropriate combination thereof.

To generate first data set 510, the base structure 501 is perturbed a desired number of times (e.g., 1000 repetitions) by applying first degree of perturbations 502, wherein the first degree of perturbations 502 are linear translations within a fixed pixel dimension (28×28 in the present 2-dimensional example) and a rotation angle within a first angle range is applied to each repetition of the linearly displaced base structure. Further, a minimum Gaussian noise may be applied to each pixel square area for each repetition in the first data set. A first distribution of the first data set 510 may have a mean first standard deviation (SD) based on variations in linear translation, rotations of the base structure, and added image noise (also known as Gaussian noise, or using other mathematical distributions that can represent stochastic processes).

To generate second data set 512, the base structure 501 may be perturbed the desired number of times by applying second degree of perturbations 504 that include rotations of the base structure and added image noise in addition to linear translations within the fixed pixel dimension. Further, a second mean amount of linear translation for the second data set 512 may be maintained the same as a first mean amount of linear translation for the first data set 510, while a ratio of a second mean rotation angle of the second data set 512 with respect to a first mean rotation angle of the first data set 510 is set at 3.0. Thus, the second mean rotation angle is greater than the first mean rotation angle. Furthermore, the ratio of second Gaussian noise of the second data set 512 with respect that of the first data set is increased to 2.0. Thus, an amount of Gaussian noise added to each pixel square is greater for the second data set 512 than the minimum Gaussian noise applied to the first data set 510. As a result, the second degree of perturbations applied to the second data set is greater than the first degree of perturbations applied to the first data set, and consequently, a second distribution of the second data set has a second mean SD that is greater than the first mean SD of the first data set.

To generate third data set 514, the base structure 501 is perturbed for the desired number of times by applying third degree of perturbations 506 that include rotations of the base structure and added image noise in addition to linear translations within the fixed pixel dimension. A third mean rotation angle and added amount Gaussian noise for the third data set 514 are increased to 9.0 and 3.0 with respect to the first data set, while a third mean amount of linear translation for the third data set 514 may be maintained the same as the first mean amount of linear translation. Thus, the third degree of perturbations applied to the third data set is greater than the first degree of perturbations applied to the first data set and the second degree perturbations applied to the second data set. As a result, a third distribution of the third data set has a third mean SD that is greater than the second mean SD and the first mean SD.

To generate fourth data set 516, the base structure is perturbed for the desired number of times by applying fourth degree of perturbations 508 to the base structure. Similar to the first, second, and third degree perturbations, the fourth degree perturbations 506 include rotations of the base structure, added image noise, and linear translations within the fixed pixel dimension. A fourth mean rotation angle and added amount Gaussian noise for the fourth data set 516 are increased to 13.0 and 4.0 with respect to the first data set, while a fourth mean amount of linear translation for the fourth data set 516 may be maintained the same as the first mean amount of linear translation. Thus, the fourth degree of perturbations applied to the fourth data set is greater than the first, second, and third degree perturbations. As a result, a fourth distribution of the fourth data set 516 has a fourth mean SD that is greater than the third mean SD, the second mean SD, and the first mean SD.

Taken together, the mean rotation angle is changed between the four sets in a relative ratio: [1.0, 5.0, 9.0, 13.0], and the Gaussian noise is changed with relative mean standard deviations: [1.0, 2.0, 3.0, 4.0]. However, the mean linear translation is the same for all four sets in order to allow the trained model to learn miss-registration of compared structures in any case.

For the strategy of few-shot learning it is useful to construct a training set (such as the first, second, third, and fourth data sets 510, 512, 514, and 516, for example) of several or many different base structures (e.g., base structure 501 in the above example), and for each base structure to generate relatively small random variations, which will be considered during the training process as belonging (identical) to the same type of their un-perturbed structure (e.g., base structure 501). As discussed above, structure perturbations can be related to random linear translations, rotations of the base structures, resizing, and added image noise (either separately or together). Further, a degree (the level) of random perturbations is changed (i.e. from low level to high level in the above example) for several different data sets each of which is used to train a corresponding CNN model. The parameters which control the level of random perturbations such as a SD of the distribution of linear base structure translation along a random axis, a SD of angle distribution of small rotation along a random axis, a SD of the resizing factor (e.g. between 0.9 to 1.1), and so on may be adjusted for each data set in order to generate sufficient variation among the data sets. It will be appreciated that the control parameters may be changed for the different data sets while using the same computational process of generating the random perturbations.

As will be further described below, each data set with a different perturbation level may be used as inputs to train a corresponding CNN model. When the perturbations are low, the trained model has a high chance to well discriminate between the different base structure types. When the perturbations are sufficiently high, the trained model may not discriminate between the different base structures, and hence, their distributions in the network output space may partially overlap.

In some embodiments, one or more hyperparameters (a parameter whose values is set prior to the training process)

of the model for lesion comparison may be tuned and selected (that is, during the detailed algorithm construction) to give the optimal clinically relevant information. As an example, such hyperparameters may include the dimensions and voxel resolution of the input image, the number of trained models based on desired comparison accuracy, the construction of the initial un-perturbed base structure set based on the type of imaging modality and evaluated disease, etc. However, it will be appreciated that by generating training data sets as discussed above and by training plurality of CNN models with the generated data sets, a number of hyperparameters is reduced. As an example, there is no need to give in advance (prior to the training process) specific ranks to the different base structures.

In this way, a plurality of training data sets may be generated by applying different degrees of perturbations to each of the plurality of training data sets. By generating training data sets as discussed herein, the need to collect large clinical data sets for model training is reduced.

Returning to FIG. 4, upon generating plurality of training data sets, each training data set is used as input to train each neural network model. As indicated at 420, the first training data set with first degree perturbations may be used as inputs to train a first neural network model; as indicated at 422, the second training data set with second degree perturbations may be used to train a second neural network model; and as indicated at 424, the third training data set may be used as input to train a third neural network model, and so on up to the $n^{th}$ training data set is used as input to train a $n^{th}$ neural network model, as indicated at 426. Each neural network model may have the same base architecture, although each model may be trained with a different training set. The neural network architectures for training may be a network that can learn and infer similarity and differences between two inputs such as a Siamese network architecture, a triplet network architecture, a matching network architecture, a relation network architecture, or a prototypical network architecture. An example Siamese network architecture is shown at FIG. 2. Since each network is trained with a different training data set (that is base structures with different levels of perturbations), an output of each neural network model is different. Details of the neural network model output will be further elaborated below with respect to FIGS. 6, 7B, 8, 9, and 10.

Figure 6:
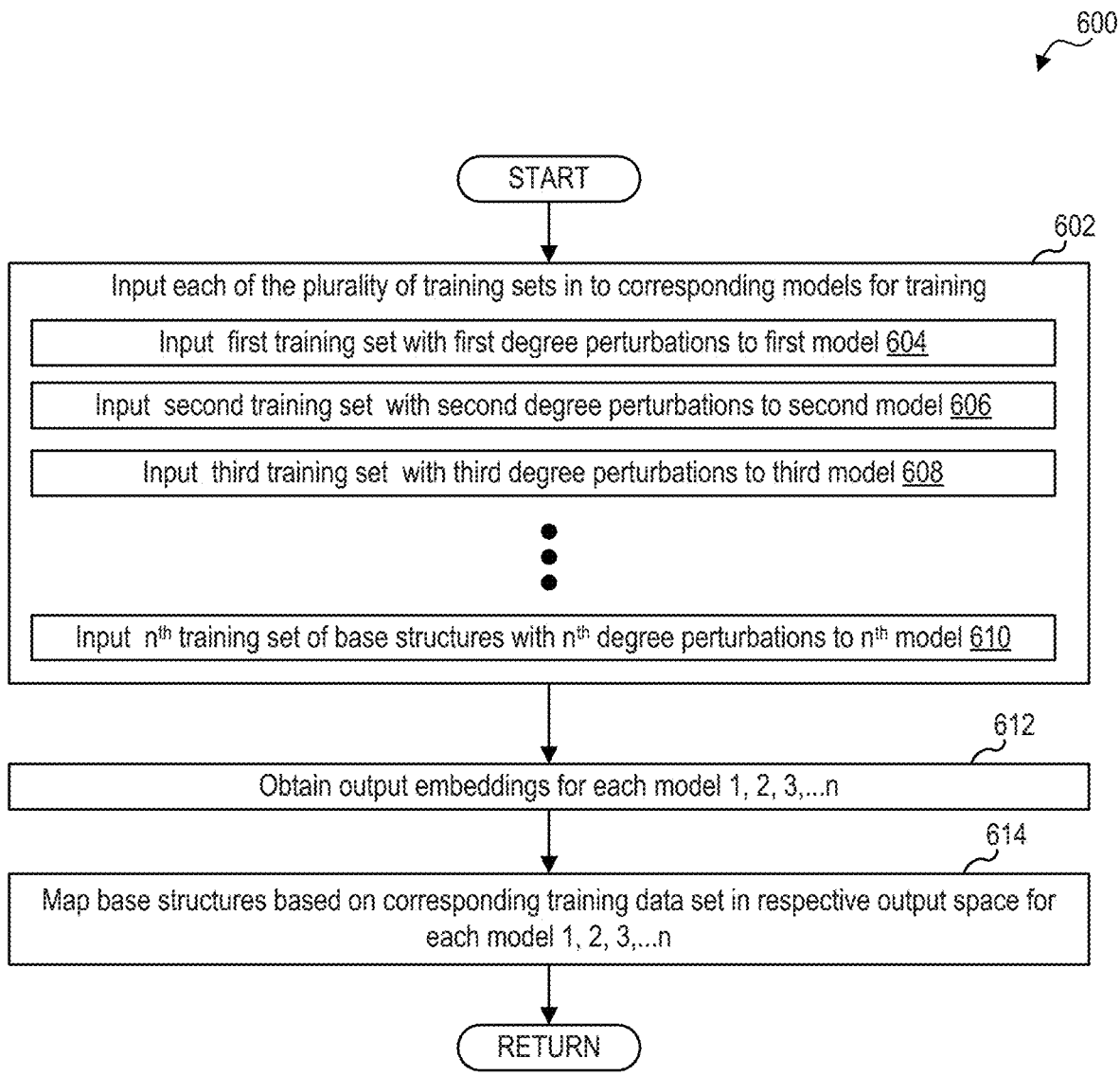
FIG. 6 is a high-level flow chart illustrating a method for training a plurality of neural networks with a plurality of base structure data sets, according to an exemplary embodiment.
Figure 7A:
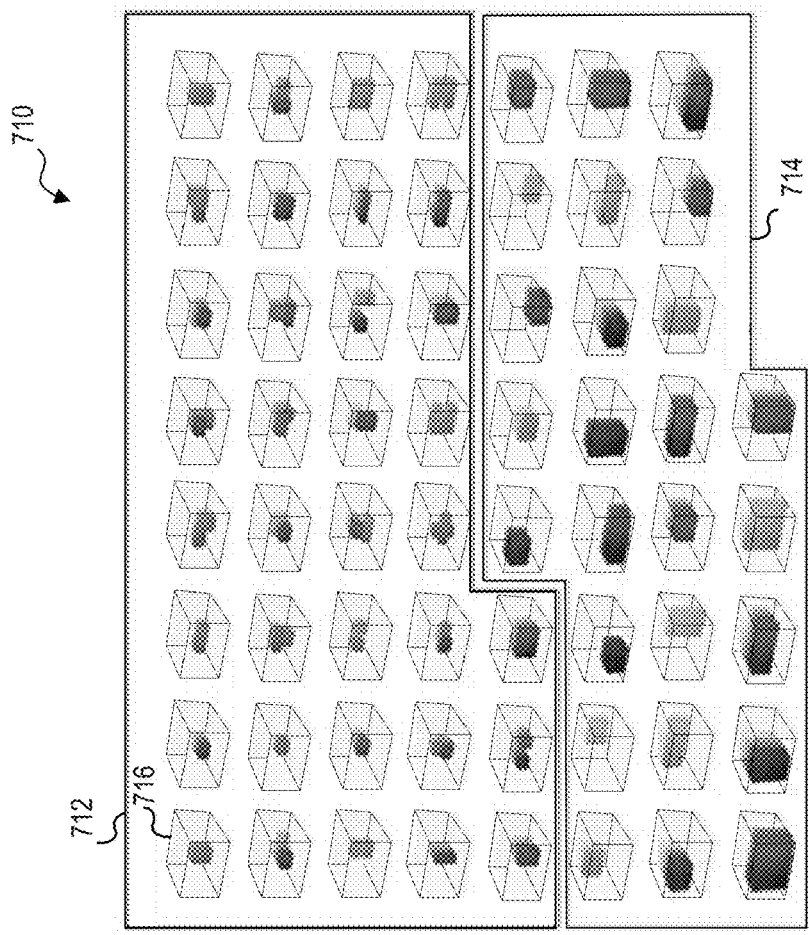
FIG. 7A shows an example data set of synthetic base structures before application of perturbations, according to an exemplary embodiment.

Turning to FIG. 6, it shows a high-level flow chart illustrating a method 600 for training a plurality of neural network models of a deep learning model, such as the first neural network model, the second neural network model . . . the $n^{th}$ neural network model of the deep learning model 201a discussed at FIG. 2, with the plurality of generated training data sets, such as the first, second, third, . . . $n^{th}$ training data sets discussed with respect to FIG. 4. Method 600 may be implemented based on instructions stored in non-transitory memory, such as non-transitory memory 106 of processor 104 of the image processing system 31 described at FIG. 1, an edge device connected to the image processing system, a cloud in communication with the image processing system, or any appropriate combination thereof.

Method 600 begins at 602. At 602, each of the plurality of training sets, such as the training sets generated at FIG. 4, are used as inputs to train each of plurality of neural network models. Thus, the number of models may be based on a number of training sets such that each model is trained with a different training set, where each training has a different perturbation level. Further, each of the plurality of neural network models may have a same network architecture. The network architecture may be a type of convolutional neural-network (CNN) based on models that are responsible for discriminating (or separating) between different structures. Specifically, the neural network model may utilize any of a few-shot learning, a single-shot learning, one-shot learning, or zero-shot learning protocols for training purposes. The advantage of the above-mentioned protocols is that a computational model can be trained on a relatively small set of known examples and can classify or discriminate between new input types that were not used for the training. The specific network and training architectures may be any of siamese networks, triplet networks, matching networks, relation network, and prototypical networks that may be constructed and trained using any algorithmic technique of few-shot learning, single-shot learning, one-shot learning, or zero-shot learning.

Although these techniques and network architectures can generally classify or discriminate between different structures, a mechanism to determine by how much any two structures are different on a given scale, which is important for medical follow-up analysis, is provided by methods described herein with respect to FIGS. 3, 4, 6, 8, 9, and 11.

Returning to method 600, at 604, the method 600 includes providing the first training data set with first degree perturbations as input to a first neural network model. Further, at 606 and at 608, method 600 includes providing the second and third training data sets (having second and third degree perturbations respectively) as inputs into second and third neural network models. Similarly, each of the remaining training data sets, up to $n^{th}$ training data set (as indicated at 610), may be used as input into corresponding neural network models. An example training method is described below with respect to siamese networks, however, it will be appreciated that any network architecture that can implemented to discriminate between two images, such as triplet network architecture or prototypical network architecture, may be employed. Further, each model may have the same network architecture so that the output embeddings can be evaluated for each training data set and the corresponding trained model.

Briefly, a siamese network architecture comprises a first convolutional neural network (CNN) and a second convolutional neural network. The first and the second CNN of a siamese network have the same architecture and are essentially copies of each other. Further, the first and second CNNs may share the same parameters. Each of the first and second CNNs include a sequence of convolutional layers, where each layer may use a desired filter size and a desired stride. Each of the first and second CNNs may then apply a rectified linear unit (ReLU) activation function to output feature maps. In some examples, optionally, max-pooling with a second desired filter size and stride may be applied. The units in the final convolutional layer may be subsequently flattened before forming a fully connected layer having d-dimensions, where "d" is a number of dimensions and is based on optimization that balances between high capability of training structure differentiation to minimizing non-linearity which enables the task of new structure differentiation. Finally, output encodings (also referred to as embeddings) of input features may be mapped in the d-dimensional output space.

When using a siamese network model, two inputs, a first input and a second input, may be used for each model. Specifically, for a neural network model with a desired degree of perturbation, in one instance the first input may include a first training structure sample related to a random perturbation with the desired degree of a randomly selected base structure type, and the second input may include a second training structure sample related to a different random perturbation (of the same desired degree of perturbation) of the same selected base structure type. In this instance, the loss function of the trained model will be based on the provided information that the two inputs are of the same type. In another instance, the first input may include the first training structure sample related to the random perturbation with the desired degree of a randomly selected base structure type, and the second input may include a third training structure sample related to the random perturbation (of the same desired degree perturbation) of a different selected base structure type. In this instance, the loss function of the trained model will be based on the provided information that the two inputs are of different types. For the $i^{th}$ neural network model, the training is performed with the corresponding $i^{th}$ training data set with $i^{th}$ degree of perturbation, where i=1, 2, 3 . . . n, and n is the total number of training data sets. Each neural network model may be trained to recognize perturbations of an un-perturbed base structure as belonging to the same un-perturbed base structure. Example deep learning protocols that may be used for training include few-shot learning, one-shot learning, and zero-shot learning. An output of each model may include embeddings of the first input and the second input in the output space.

Accordingly, at 612, method 600 includes obtaining output embeddings for each of the plurality of neural network models. The output embeddings are outputs of the corresponding neural network model. Thus, the output embeddings for each of the plurality of neural networks is based on a corresponding training data set used as input for training.

Next, at 614, method 600 includes mapping base structure embeddings in the respective output space for each of the plurality of neural network models. Specifically, each trained neural network model includes an output space, wherein the input base structures and corresponding perturbations are mapped onto the output space. A number of dimensions of the output space for each neural network model may be based on optimization that balances between high capability of training structure differentiation to minimizing non-linearity which enables the task of new structure differentiation. An example mapping of input base structures and its perturbations in a two-dimensional output space is illustrated at FIG. 7B below.

Upon mapping the base structures and its perturbations in each output space of each neural network model, method 600 returns. In this way, each of the plurality of neural network models may be trained with a corresponding set from the plurality of training data sets so as to generate a plurality of embedding maps (based on the plurality of neural network models) of the base structures and its perturbations.

Turning to FIG. 7A, an example data set 710 of un-perturbed base structures is shown. The data set 710 includes 61 base structures, where each base structure is shown embedded within a box 716 of 14×14×14 voxels. The data set 710 includes inner structures 712 as well as edge structures 714. Inner structures 712 include base structures in one or more of the central regions of a selected box size of the box of voxels, and edge structures 714 include base structures close to or attached to the edges of the box of voxels. Further, while the present example shows illustrates each structure embedded within a 14×14×14 box of voxels, other voxel dimensions, such as 28×28×28 are also within the scope of the disclosure. The 61 base structures in the data set 210 may be synthetic structures, natural lesion motifs, or any combination thereof. The synthetic structures may be based on known lesions structures, for example.

For purposes of training a neural network model, such as first neural network model, second neural network model, . . . $n^{th}$ neural network model, a training data set having a desired number of perturbations (e.g., 1000 different random perturbations) for each base structure may be generated. The training data set may be used as input to train the neural network model to recognize perturbations of an un-perturbed base structure as belonging to the same un-perturbed base structure. An example output map 750 of a trained neural network model is shown at FIG. 7B. For illustration purposes, the output map 750 is shown with two dimensions, including network embedding 1 and network embedding 2. However, a number of dimensions of the output space may be greater (6 or 16, for example). In one exemplary embodiment, the number of dimensions of the output space may be based on optimization that balances between high capability of training structure differentiation to minimizing non-linearity which enables the task of new structure differentiation, such as one or two orders of magnitude smaller than the number of training base structures. The output map 750 at FIG. 7B shows mapping of each base structure shown in FIG. 7A and the corresponding perturbations creating a distribution cloud in the output map 750 of a trained network model. Thus, each distribution cloud is a grouping of perturbations of a specific base structure, with similar structural motifs arranged closer to each other.

In this way, each trained neural network model (trained with a training data set) has a d-dimensional output space with base structures and corresponding perturbations mapped onto the output space. Thus, the output of each trained neural network model includes representations of its input. For example, a first output d-dimensional space of a first trained neural network model, trained with a first training set (having first degree perturbations) includes encoding of the first training set. Similarly, a second d-dimensional output space of a second trained neural network model, trained with a second training data set (having second degree perturbations) includes encodings of the second training data set mapped onto the second output space, and so on up to "n" output mappings for $n^{th}$ trained network can be generated. Overall, a plurality of network output maps may be generated for each of the plurality of neural network models, where each neural network model is trained on a training set having a different degree of perturbation.

Turning to FIG. 8, a high-level flow chart illustrating a method 800 for inference with a trained deep learning model including a plurality of trained neural network models is shown. The plurality of trained neural network models may include the plurality of neural network models such as the first neural network model, second neural network model . . . $n^{th}$ neural network model discussed at FIG. 2 that have been trained as discussed above with respect to FIG. 6 with the plurality of generated training data sets, such as the first, second, third, . . . $n^{th}$ training data sets generated as discussed with respect to FIG. 4. Specifically, the method 800 illustrates testing each of the plurality of network models with new data. Method 800 may be implemented based on instructions stored in non-transitory memory, such as memory 106 of processor 104 of the image processing system 31 described at FIG. 1, an edge device connected to the image processing system, a cloud in communication with the image processing system, or any appropriate combination thereof. Briefly, for data inference (that is, the process of testing new data with a model which is already trained) of the tested lesions, two input structures (baseline and follow-up) are passed separately through each of the plurality of trained models and the corresponding network outputs of the baseline and follow-up structures are obtained. That is, network encodings of the baseline and follow-up structures mapped on output space of each of the plurality of trained models are obtained. The algorithm may then determine if the baseline and the follow-up structures are similar or different and the rank of difference, based both on a distance between the mapped embeddings of the two lesions (baseline and follow-up) in the output space and on the statistical distribution widths of the discriminated structures in the several models.

Method 800 begins at 802. At 802, method 800 includes acquiring a baseline image and a follow-up image. The baseline image may be obtained during a first baseline medical scan, and includes a lesion structure imaged during the first baseline medical scan. The follow-up image may be obtained during a second follow-up medical scan, and includes the lesion structure imaged during the second follow-up medical scan. The lesion structure in the baseline image and the lesion structure in the follow-up image may each be embedded within a box of voxels. In some embodiments, 2 dimensional sub-regions of the lesion structures may be considered. Further, the lesion structure may be positioned/embedded anywhere within the box of voxels, exact centering may not be necessary.

In one exemplary embodiment, the first baseline medical scan and the follow-up scan may be performed using a functional imaging modality, such as SPECT or PET. Evaluation of structural similarity of anatomical structure using medical scan images (baseline and follow-up) obtained using other imaging modalities, such as CT, MRI, and ultrasound are also within the scope of the disclosure.

Next, at 804, method 800 includes inputting the baseline image and the follow-up images into each of the plurality of trained neural network models. That is, for each trained neural network model (each model trained with a different training set having different perturbations of the base structure set), the baseline image and the follow-up image are used as inputs to evaluate structural differences between the baseline and the follow-up image. Specifically, the baseline image and the follow-up images may be passed through each of the first trained neural network model, the second trained neural network model, the third trained neural network model, and so on until the baseline image and the follow-up image are passed through all of the trained neural network models.

Next, at 806, the method 800 includes obtaining output encodings of the baseline and the follow-up images in each output space of each of the plurality of the trained networks. Specifically, after passing the baseline and the follow-up images through a first trained neural network model, a first baseline encoding and a first follow-up encoding (of the input baseline and follow up images respectively) may be obtained. Similarly, after passing the baseline and the follow-up images through a second neural network model, a second baseline encoding of the input baseline image and a second follow-up encoding of the of the input follow-up image may be obtained. In this way, after passing the baseline and the follow-up images through each of the plurality of trained neural networks, corresponding output encodings of the baseline and follow-up images may be obtained.

Continuing on at 808, the method 800 includes mapping the baseline and the follow-up images with respect to the mapped base structures in the corresponding output space for each trained model. Specifically, the first baseline encoding and the first follow-up encoding may be mapped onto the first output space of the first trained neural network model, where the first output space includes mappings of the base structures from the first training data set used as input for training the first neural network model. Similarly, the second baseline encoding and the second follow-up encoding may be mapped on the second output space of the second trained neural network model having mappings of the second corresponding base structures from the second training data set used for training the second neural network; the third baseline encoding and the third follow-up encoding may be mapped on to the third output space of the third trained neural network model having mappings of the third corresponding base structures from the third training data set used for training the third neural network; and so on until the $n^{th}$ baseline encoding and the $n^{th}$ follow-up encoding are mapped on to the $n^{th}$ output space of the $n^{th}$ trained neural network model having mapping of the $n^{th}$ corresponding base structures from the $n^{th}$ training data set used for training the $n^{th}$ neural network. In this way, mappings of the baseline image and the follow-up image are obtained in each output space of each of the plurality of trained neural networks.

Upon passing the baseline image and the follow-up image through each of the plurality of trained neural network models and obtaining baseline and follow-up encodings in each output space of each of the plurality of trained neural networks, method 800 proceeds to 810. At 810, method 800 includes evaluating the baseline and the follow-up mappings with respect to the corresponding base structure mappings in each output space of each of the plurality of trained neural network models. Details of evaluating the baseline and follow-up encodings with respect to the corresponding base structure mappings in each output space will be discussed below with respect to FIG. 9. Briefly, evaluating the baseline and follow-up images with respect to the corresponding base structure mappings may include determining if the baseline and the follow-up structures (from the baseline and the follow-up images respectively) are similar or different, and further includes determining the rank of difference, based on a distance between the mapped encodings of the baseline and follow-up images in the output space, and further based on corresponding statistical distribution widths of the discriminated structures in each of plurality of the trained neural network models.

Turning to FIG. 9, it shows a high-level flow chart illustrating a method 900 for evaluating differences between the baseline and the follow-up images based on the baseline and the follow-up encodings mapped in each output space of each of the plurality of trained neural network models. It will be appreciated that the evaluation of the differences between the baseline and the follow-up images may be performed for each model separately. For example, due to the way the plurality of neural network models are trained, the mapping arrangement of the learned structures in the several models may be different between them. Therefore, the inference may be done with each model separately. Further, it may be noted that the mapped distribution sizes can be different for different perturbed base structures (depending on the structural configuration of the base structure), even if the perturbation level is the same. Method 900 may be implemented based on instructions stored in non-transitory memory, such as non-transitory memory 106 of processor 104 of the image processing system 31 described at FIG. 1, an edge device connected to the image processing system, a cloud in communication with the image processing system, or any appropriate combination thereof.

Method 900 begins at 902. At 902, the method 900 includes determining distances between baseline and follow-up encodings in each output space of each neural network model. While mapping of the base structures generate a distribution cloud for each base structure (since each base structure is perturbed multiple number of times), each of the baseline encoding and the follow-up encoding are represented as points (since there is only one structure for the baseline and one structure for the follow-up) in each output space. Thus, a mapping of the baseline encoding in an output space will be alternatively referred to as a baseline point and a mapping of the follow-up encoding in an output space will be alternatively referred to as a follow-up point.

Determining distance between the baseline and the follow-up encodings in each output space includes determining an absolute difference between the mapped baseline encoding and the mapped follow-up encoding. For example, if the baseline encoding is represented as f(baseline), the follow-up encoding is represented as f(follow-up), and distance between the baseline and the follow-up encoding is represented as S, then, $$S_i = |f(\text{baseline})_i - f(\text{follow-up})_i|,$$

Where i is an order of trained neural network model, and i=1, 2, 3, . . . n

In one exemplary embodiment, the distance S between the baseline and the follow-up encoding may be a Euclidean distance. Other distance metrics, such as cosine, chebychev, etc., for determining distance between baseline and the follow-up encoding in multi-dimensional space may also be employed, and are within the scope of the disclosure.

For example, $S_1$ is a first distance between the baseline encoding and the follow-up encoding in the first output space of the first trained neural network model; $S_2$ is a second distance between the baseline encoding and the follow-up encoding in the second output space of the second trained neural network model; $S_3$ is a third distance between the baseline encoding and the follow-up encoding in the third output space of the third trained neural network model; and so on . . . up to $S_n$, where $S_n$ is a $n^{th}$ distance between the baseline encoding and the follow-up encoding in the $n^{th}$ output space of the $n^{th}$ trained neural network model.

Next, at 904, method 900 includes identifying one or more mapped base structures in the vicinity of each of the mapped input and follow-up encodings in each output space for each trained neural network model (that is, in the vicinity of each of the baseline point and the follow-up point mapped in each output space for each trained neural network model). Specifically, for the first trained model, one or more base structures in the vicinity of each of the baseline and the follow-up points in the first output space of the first trained neural network model, may be identified; for the second trained model, one or more base structures in the vicinity of each of the baseline and follow-up points in the second output space of the second trained neural network model may be identified, for the third trained model, one or more base structures in the vicinity of each of the baseline and follow-up points may be identified; and so on, up to one or more base structures in the vicinity of the baseline and follow-up points in the $n^{th}$ output space of the $n^{th}$ trained neural network model may be identified.

In one exemplary embodiment, the one or more mapped base structures in the vicinity of each of the baseline point and the follow-up point may be identified by implementing a K-nearest neighbor (KNN) approach for each trained model, wherein a value for K may be selected, and distances of the baseline and follow-up points with respect to K nearest points (which in the present example may be centroids of the base structure distribution) may be determined, and the K nearest neighbors may be identified. It will be appreciated that the determination of the K nearest neighbors may not be directed to a specific classification of the baseline and the follow-up points, rather the K nearest neighbor approach may be used to identify and select one or more base structures in the vicinity of the baseline and the follow-up points in the output space for each neural network model. Alternatively, the 'Mahalanobis distance' approach for measuring the distance between a point and a distribution can be used to identifying the base structures in the vicinity of the baseline and follow-up points in each output space In one example, the value of K (that is, the value that determines a number of the one or more structures in the vicinity) may be based on the data set used to train the particular neural network model, and more specifically, based on a degree of perturbations of the training data set used to train the neural network model. For example, as a degree of perturbation increases, a number of the one or more structures in the vicinity may also increase Next, method 900 proceeds to 906. At 906, method 900 includes calculating a mean distribution size of the one or more base structures identified in the vicinity of the baseline and the follow-up input points in each output space for each trained neural network model. For example, for the first trained model, if K number of base structures (Bj, where j=1, 2, 3 . . . K) are identified, and a distribution size for each base structure Bj is estimated by a standard deviation value (SDj, where SD is the standard deviation, and j=1, 2, 3, . . . K), a first mean distribution size may be represented by W1, where $W1 = 1/k \Sigma_{j=1}^{K} SDj$. Similarly, mean distribution sizes W2, W3, . . . Wn for each of the trained neural network models may be determined, where W2 is the second mean distribution size of the one or more vicinity structures identified for the second trained model, W3 is the third mean distribution size of the one or more vicinity structures identified for the third trained model, and Wn is the $n^{th}$ mean distribution size of the one or more vicinity structures identified for the $n^{th}$ trained model.

Continuing on to 908, method 900 includes for each trained model, calculating a difference between 1) The distance between the baseline point and the follow-up point (determined at 902) and 2) The corresponding mean distribution size (determined at 906). Thus, for the first trained model, a first difference D1 may be determined, where the first difference is calculated between 1) The first distance S1 between the baseline point and the follow-up point, and 2) The first mean distribution size W1. Thus, the first difference D1 may be represented as, D1=S1−W1. Generalizing the above to "n" number of trained neural network models, the difference Di=Si−Wi, where i=1, 2, 3 . . . n.

Upon calculating the difference for each trained neural network model, method 900 proceeds to 910. At 910, method 900 includes identifying a series of trained neural network models including one or more models where the difference between the distance between the baseline point and the follow-up point, and the corresponding mean distribution size is less than or equal to zero. In other words, method 900 includes identifying the series of trained models where the distance between the baseline and follow-up points is equal to or smaller than the mean distribution size of the mapped structures in the vicinity of the baseline and the follow-up points.

Next, at 912, method 900 includes identifying the neural network model trained with the lowest degree of perturbation. Upon selecting the neural network model trained with the lowest degree of perturbation, method proceeds to 914.

At 914, method 900 includes calculating a similarity index (SI) based on a serial number of the identified lowest perturbation model in the series of trained models. Specifically, the serial number of the identified/selected neural network model may be based on the order number of the selected neural network, where the order corresponds to the degree of perturbation of the base structures used for training the selected model. The similarity index is an indication of structural similarity or difference between the baseline and the follow-up images, where a larger index is due to a greater serial number (that is, greater order number) of the identified lowest perturbation model, and thus indicates larger structural difference between the baseline and the follow-up images. A smaller index is due to a lower serial number of the identified lowest perturbation model, and thus indicates smaller structural difference between the baseline and the follow-up images. It may be noted that the serial number (or order) may correspond to a degree of perturbation of base structures used to train the selected model. Thus, the degree of perturbation of the selected trained model corresponds to the level of structural change between the baseline and the follow-up images. In this way, the similarity index is standardized based on the degree of perturbation of a plurality of base structures where the degree of perturbation corresponds to the change between the baseline and follow-up images.

As an example, if the degree of perturbation (or order/serial number) of the selected trained model is greater, it may be an indication that the follow-up image has a greater structural perturbation compared to the baseline image. Consequently, the structural similarity index may indicate a greater structural difference between the baseline and the follow-up images. As another example, if the degree of perturbation (or order/serial number) of the selected trained model is smaller, it may be an indication that the follow-up image has a smaller structural perturbation compared to the baseline image. Consequently, the structural similarity index indicates a smaller structural difference between the baseline and the follow-up images.

In this way, inference is performed with each model separately, and a two-structure (baseline and follow-up structure) compared difference level is determined by identifying the neural network model in which the distance between the baseline and the follow-up points in the output space of the identified model is equal to or smaller than the mean distribution size of the one or more mapped base structures in the vicinity of the baseline and the follow-up points, and determining the similarity index based on the neural network model identified.

While method 900 illustrates comparison of two structures, it will be appreciated that the method can be used to compare more than two structures. For example if three structures (e.g., baseline structure imaged during baseline imaging, first follow-up structure imaged during first follow-up imaging, and a second follow-up structure imaged during a second follow-up imaging), each of the three structures may be mapped onto each trained network output space, and for each of the first and second follow-up structures, similarity indices may be calculated with respect to baseline and with respect to each other. Similarly, any number of structures to be evaluated may be input into trained networks, and pairwise comparison between any two internal anatomical structures may be performed.

In an exemplary embodiment, lesion severity ranking based on a priori tagging/ranking may be integrated into the method. Details of evaluating one or more new structures based on a priori ranked structures will be further described with respected to FIGS. 11 and 12.

It may be noted that during the model training the similarity level between different structures are learned automatically through the process of model optimization. As a result, specific ranks to the different base structures may not be given in advance, and further, there is no need to manually select and design specific lesion features. Consequently, annotation workload is significantly reduced.

Upon determining the similarity index, the method 900 proceeds to 916. At 916, the method 900 includes providing a first indication if the baseline and the follow-up images are similar based on the similarity index, and further includes providing a second indication of a rank of difference (that is, the similarity index value), and further includes providing a third indication of change direction (e.g., if two subsequent follow-up images are compared to the baseline, the third indication may indicate if the structure change is increasing). For example, the first, the second, and the third indications may be displayed on a user interface, such as display device 33 at FIG. 1.

At FIG. 10 an example embedding map set 1000 including three output embedding maps in corresponding output space of three neural network models trained with three training data sets having different levels of perturbations of a set of base structures is shown. Further, inference results showing mapping of two lesion structures onto each of the three network output space are shown.

Mapping 1000 shows a first embedding map 1001 of a first neural network model trained with a first training set having a first perturbation level for the base structures, a second embedding 1020 of a second neural network trained with a second training data set having a second perturbation level greater than the first perturbation level, and a third embedding 1030 of a third neural network model trained with a third training data set having a third perturbation level greater than the second perturbation level.

Each map 1001, 1020, and 1030 is represented in two dimensions, for one or more of visualization and inference purposes. Although the present example shows network embeddings in two dimensional space, it will be appreciated that the output embeddings from each neural network model has high-dimensionality (e.g., 6 or 16 dimensions), which may be based on the data set, for example, and as such, dimensionality is reduced to two (or three in other example embodiments) for one or more of visualization and inference purposes. That is, dimensionality of embeddings of base structures in the output space of each neural network model is reduced (from high-dimensional output of neural network model to two dimensions) in order to enable visualization of the distribution of base structure mapping in each neural network model output space. Thus, in each map 1001, 1020, and 1030, x-axis represents a first dimension of base structure embeddings in Euclidean space for the corresponding model, and the y-axis represents a second dimension of base structure embeddings in Euclidean space for the corresponding model.

In the present example, six base structures are illustrated. It will be appreciated that a number of base structures may be sufficiently large to account for various structural motifs as discussed herein. The variations in base structure (due to perturbations of base structures in the training data set) generate a distribution cloud for each base structure, and thus the base structure embeddings and the variations in the base structure embeddings are presented by circles, where each circle represents embeddings of a base structure and its corresponding structure perturbations. Thus, each map 1001, 1020, and 1030 shows six base structure embeddings 1002, 1003, 1004, 1005, 1006, and 1007, each representing embeddings of a base structure and its perturbations. As the degree of perturbations increases, a distribution of the base structure and the corresponding perturbation structure embeddings in the output space increases. For example, for the first neural network model trained with the first degree of perturbation (first degree<second degree<third degree), the perturbations are grouped closer together around the base structure, and thus, the (six) circles representing the (six) base structures and its perturbation distribution are smaller. For the second neural network model trained with the second degree of perturbation greater than the first, the base structure and the corresponding perturbation structure embeddings are more widely distributed, and hence, the circles representing the base structure and its perturbation distributions are larger than the corresponding distribution in the first output space of the first neural network. This follows that the base structure and the corresponding perturbation structure distributions in the third output space of the third neural network trained with the base structures having the greatest level of perturbation has the largest distribution, and hence the base structure distributions are represented by circles that are larger than the corresponding distributions in the second output space.

To illustrate further, consider embeddings 1004 including a base structure embedding and its corresponding perturbations embeddings, in the first (two-dimensional) output space of the first neural network model, a first distribution of the embeddings are represented by circle 1004. In the second output space, a second distribution of the embeddings are greater, and thus diameter of the circle 1004 is greater in the second output space than in the first output space. Further, as the third distribution in the third output space is the greatest, the circle 1004 has the largest diameter.

While the present example illustrates embeddings of six base structures, the mapping can be extended to the set of base structures used for training. Thus, for each neural network model, its output space includes embeddings of each base structure and its perturbations, where a distribution of the embeddings of each base structure and its perturbations is based on a degree of perturbations of the training data set.

Further, each embedding map 1001, 1020, and 1030 includes a first lesion point 1010 and a second lesion point 1011 that are embeddings of a first lesion structure and a second lesion structure obtained after passing the first and second lesion structures through each of first, second, and third trained neural network models. For example, during inference of the trained neural network models, a baseline image of a structure taken during an initial medical scan, and a follow-up image of the structure taken at a different later time point during a follow-up medical scan, may be evaluated to determine one or more of a similarity, a level of similarity, and a direction of change. The baseline structure and the follow-up structure images are mapped onto each output space of each trained neural network model.

In this example, the first lesion structure and the second lesion structure are used for inference with the first, second, and third neural network models. As such, embeddings 1010 and 1011 are generated and mapped in each output space. The first and the second lesion structures may then be evaluated based on a distance between embedding points 1010 and 1011 in each of the first, second, and third output space, and based on mean distribution sizes of each of the embeddings, 1002, 1003, 1004, 1005, 1006, and 1007, in each output space for each of the three models. As discussed above, the mean distribution size may be estimated based on standard deviation of the distribution of the embeddings. Thus, for each embedding 1002, 1003, 1004, 1005, 1006, and 1007 the corresponding mean distribution size increases with increasing order of perturbation for the neural network model. As such, for each embedding, 1002, 1003, 1004, 1005, 1006, and 1007, the corresponding mean distribution size is lowest in the first output space of the first neural network model, greatest in the third output space of the third neural network model, with the second neural network model in the middle.

In order to determine difference between the first and the second lesion structures, the lowest model level in which a distance between the first and the second lesion embeddings 1010 and 1011 is equal or smaller than a mean distribution size of the nearest mapped structures (which is 1002, 1003, 1004, 1005, 1006, and 1007 in this example) may be identified. Thus, in this example, a first distance between the first and the second lesion embeddings 1010 and 1011 in the first output space of the first neural network model, a second distance between the first and the second lesion embeddings 1010 and 1011 in the second output space of the second neural network model, and a third distance between the first and the second lesion embeddings 1010 and 1011 in the third output space of the third neural network model may be determined.

Further, assuming the mapped structures in the vicinity of the first and the second lesion structures include 1002, 1003, 1004, 1005, 1006, and 1007, a first mean distribution size of the embedding distributions 1002, 1003, 1004, 1005, 1006, and 1007 in the first output space, a second mean distribution size of the embedding distributions 1002, 1003, 1004, 1005, 1006, and 1007 in the second output space, and a third mean distribution size of the embedding distributions 1002, 1003, 1004, 1005, 1006, and 1007 in the third output space may be determined. In one example, the mean distribution size is determined based on standard deviation of the distributions, and thus, the first mean distribution size may be calculated as average of standard deviations of embedding distributions 1002, 1003, 1004, 1005, 1006, and 1007 in each output space.

Upon determining the distance between embedding points 1010 and 1011 in each of the first, second, and third output space, and the mean distribution sizes of the embeddings, 1002, 1003, 1004, 1005, 1006, and 1007, in each output space, the lowest model (trained with the data set having the lowest degree of perturbations) in which the distance between the first and the second lesion embeddings 1010 and 1011 is equal or smaller than the mean distribution size of the nearest mapped structures may be identified. In this example, the third neural network model represented by embedding map 1030 may satisfy the criteria for the lowest neural network model discussed above.

Upon identifying the lowest neural network model (which is the third neural network model in this example), a similarity index may be determined based on the identified model as discussed above with respect to FIG. 9. Briefly, the similarity index may indicate a level of similarity and is based on the serial number (that is, order number indicating the degree of perturbation of the identified model) of the identified lowest perturbation model in the series of trained models.

In summary, three different neural network models are considered, each with different perturbation level (the third neural network model represented by output embedding 1030 is with the highest level). Larger circle indicates wider distribution, which is a result of larger perturbation level. Thus, third neural network model embeddings have larger circles for each of the six base structures compared to the first and the second model embeddings 1001 and 1020 respectively. The inference of the first and the second lesion structures resulted in points 1010 and 1011 in each output space, and the two-lesion compared difference level can be taken as the first (lowest) model level in which the distance between the lesion points 1010 and 1011 (in the output space) is equal or smaller than the mean distribution size of the mapped structures in the vicinity of the lesion points. The lowest level satisfying the above criteria is the third neural network model, and thus, one or more of the determination of similarity (or difference), the similarity index, and the direction of change between the first and the second lesion structures may be determined based on the selected neural network model.

Figure 11:
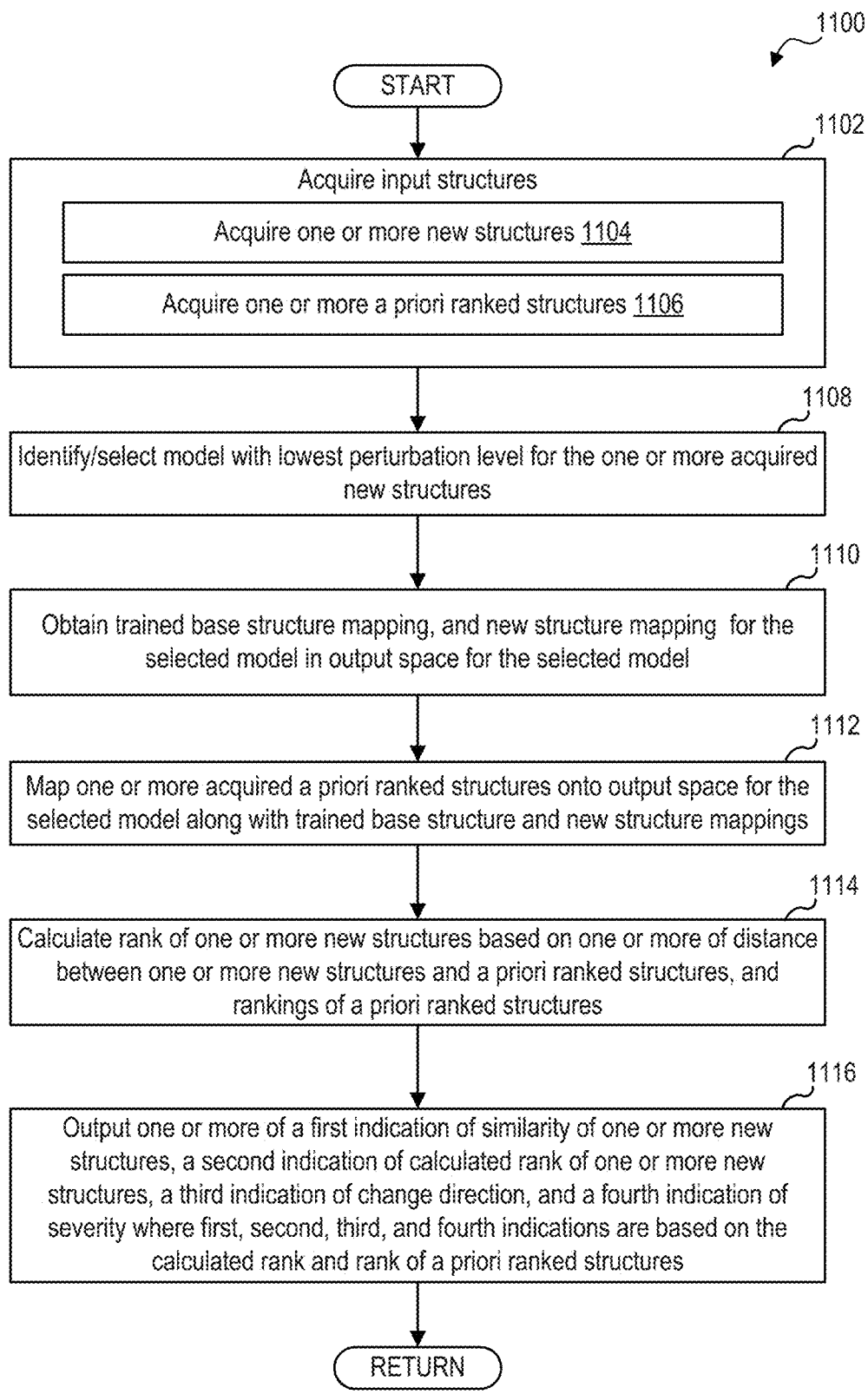
FIG. 11 is a high-level flow chart illustrating a method for determining similarity between an input structure and a follow-up structure utilizing a priori ranking in conjunction with a plurality of trained neural networks, according to an exemplary embodiment.

Turning next to FIG. 11, a high-level flow chart illustrating a method 1100 for evaluating one or more new input structures, such as new lesion structures for analysis, based on a priori ranking of known lesion structures, according to an exemplary embodiment, is shown. The evaluation of one or more new input structures may be performed with a trained deep learning model having a plurality of trained neural network models. The plurality of trained neural network models may include the plurality of neural network models such as the first neural network model, second neural network model . . . $n^{th}$ neural network model as discussed at FIG. 2 that have been trained as discussed above with respect to FIG. 6 with the plurality of generated training data sets, such as the first, second, third, . . . $n^{th}$ training data sets generated as discussed with respect to FIG. 4. Evaluating one or more new input structures may include one or more of estimating a rank of the one or more new input structures based on a small number of a priori ranked structures and a direction of change between at least two new input structures (e.g. improving or deteriorating condition). Method 1100 may be implemented by a processor, such as processor 104 of the image processing system 31 described at FIG. 1, an edge device connected to the image processing system, a cloud in communication with the image processing system, or any appropriate combination thereof.

Method 1100 begins at 1102. At 1102, method 1100 includes acquiring input structures. Acquiring input structures includes, at 1104, acquiring one or more new structures, and further includes, at 1106, acquiring one or more a priori ranked structures. The one or more new structures may include lesion structures imaged during a functional medical imaging follow-up procedure, for example. Thus, the one or more new structures may include a baseline image and one or more follow-up images. The baseline image may be obtained during a first baseline medical scan, and may include a lesion structure imaged during the first baseline medical scan. The one or more follow-up images may be obtained during one or more subsequent follow-up medical scans, and may include images of the same lesion structure but imaged during the one or more subsequent follow-up medical scans. The one or more a priori ranked structures may be independently analyzed, clinically classified and ranked by a human expert, such as a radiologist or a physician.

Further, a number of the a priori ranked structures is less than a number of base structures used for training. Furthermore, the number of the a priori ranked structures may be small and cannot be used as a training set for the network model, even with the help of data augmentation techniques.

In one example, the one or more new structures and the one or more a priori ranked structures may be input by a user via a user interface. Thus, acquiring input structures includes receiving the input structures via a user interface, such as input device 32 at FIG. 1. The one or more new structures and the one or more a priori ranked structures may be stored in non-transitory memory, such as memory 106, and retrieved by the user during the evaluation of the input structures.

Next, upon acquiring the one or more new structures, method 1100 includes, at 1108, selecting a neural network model with lowest perturbation level (also referred to as lowest model) for the one or more new structures acquired. The identification or selection of the lowest network model is discussed with respect to FIG. 8 and FIG. 9 (particularly, steps 902 to 912), and will not be repeated here for the sake of brevity. Briefly, the lowest model may be selected by identifying the model level (level based on a degree of perturbation of a training data set for the model) in which a distance (in the corresponding lowest model output space) between the one or more new structures is equal to or smaller than a mean distribution size of the nearest mapped structures. If only one new structure is provided, the lowest model can be identified based on the one or more a priori ranked structures.

Upon selecting the lowest model, method 1100 proceeds to 1110. At 1110, the method 1100 includes obtaining embeddings in the lowest model output space for the base structures in its corresponding training data set and for the one or more new structures acquired. In other words, the embeddings for the one or more new structures may be mapped on to the output space for the lowest model selected with respect to the embeddings for its corresponding training data set.

Next, at 1112, method 1100 includes mapping embeddings of the one or more a priori ranked structures on to the lowest model output space that includes the base structure embeddings and the new structure embeddings. As a result, the lowest model output space may now include 1) Embeddings for the training data set, including plurality of base structures and its perturbations (where perturbation level is the perturbation level of the training data set), 2) Embeddings for the one or more new structures acquired (at 1104), and 3) Embeddings for the one or more a priori ranked structures acquired (at 1106). Further, the lowest model output space may have high dimensionality (e.g., based on one or more of a number and variations in the unperturbed base structure data set, where greater variation of unperturbed base structures increases the dimensions and as a number of base structure increases, the dimensions may increase).

Next, upon obtaining the embeddings as discussed above, method 1100 proceeds to 1114. At 114, method 1100 includes calculating a rank of one or more new structures based on one or more of distance between one or more new structures and a priori ranked structures, and rankings of a priori ranked structures. Calculating the rank of the one or more new structures includes weighting the distances and levels of all neighboring a priori ranked lesions. Specifically, for each of the one or more new structures, distances between the corresponding new structure and each of the a priori ranked structures may be determined. Then, one or more a priori ranked structures whose distances with respect to the new structure is less than a threshold may be selected. For example, if five a priori ranked structures are mapped in the lowest model output space, and only four have distances that are less than the threshold, then the four a priori ranked structures may be selected. Upon selecting the a priori ranked structures that are closer (based on the respective distances relative to be new structure being less than the threshold) to the new structure, the rank of the new structure may be determined based on assigning weights to the distances (where shorter distances are assigned greater weightage) and the ranking (determined by an expert) of the a priori ranked structures. An example embedding map and analysis of new structures based on a priori ranked structures is described further below with respect to FIG. 12.

Upon determining the rank of the one or more new structures, method 1100 proceeds to 1116. At 1116, method 1100 includes outputting, via a display device (e.g., display device 33 at FIG. 1), one or more of a first indication of similarity of one or more new structures, a second indication of calculated rank of one or more new structures, a third indication of change direction, and a fourth indication of severity where first, second, third, and fourth indications are based on the calculated rank and rank of a priori ranked structures.

In this way, relatively small number of a priori ranked (or clinically classified) lesions can be used to estimate the ranking of a new analyzed lesion, or to estimate the amount or direction of change between two new lesions (e.g. improving or deteriorating condition).

In an exemplary embodiment, the a priori ranking may be disease specific, and thus, can provide additional information as to the status of the newly analyzed structure.

Turning to FIG. 12, an example map 1200 of embeddings output from a neural network model including embeddings of one or more a priori ranked structures is shown. Specifically, map 1200 includes embeddings in an output space of a lowest selected network model, such as the lowest model discussed with respect to FIG. 11 above is shown. As discussed above, the lowest model may be selected by identifying the model level (level based on a degree of perturbation of a training data set for the model) in which a distance (in the corresponding lowest model output space) between the one or more new structures is equal to or smaller than a mean distribution size of the nearest mapped structures.

Further, map 1200 includes an embedding of an example new lesion structure. The embedding of the new lesion structure is represented as a point, and is indicated by 1230. For purpose of one or more of visualization and inference, the output space of the lowest model network is represented in a two-dimensional Euclidean space, where x-axis represents a first dimension of base structure embeddings for the model, and the y-axis represents a second dimension of base structure embeddings for the corresponding model.

Map 1200 shows a plurality of base structure embedding, where the base structure embeddings correspond to a training data set used to train the model. Each base structure embedding is represented by a circle, as the perturbations of the base structures in the training data set creates a distribution when mapped on to the two dimensional output space. In the present example 16 base structure embeddings indicated by 1202, 1203, 12304 . . . 1217, are shown. However, it will be appreciated that the number of base structure embeddings may be based on a number of unperturbed base structures used for training.

Map 1200 further shows embeddings 1220, 1240, 1250, 1260, and 1270, each representing a mapping of each of five a priori ranked structures in the output space of the model. Specifically, 1220 is an embedding of a first a priori ranked structure (hereinafter first ranked structure), 1240 is an embedding of a second a priori ranked structure (hereinafter second ranked structure), 1250 is an embedding of a third a priori ranked structure (hereinafter third ranked structure), 1260 is an embedding of a fourth a priori ranked structure (hereinafter fourth ranked structure), and 1270 is an embedding of a fifth a priori ranked structure (hereinafter fifth ranked structure). By inference process, the five ranked structures are automatically mapped onto the network output space.

Further, each of the a priori ranked structures are assigned a rank based on independent analysis by a human expert. As an example, the first ranked structure and the second ranked structure may be each assigned a first rank with a value of 1, the third ranked structure may be assigned a second rank with a value of 2, the fourth and the fifth ranked structures may be each assigned a third rank with a value of 3, where the values of the ranks are determined based on analysis by a human expert. It may be noted that the small number of a priori ranked structures is not sufficient as a training set for the network model, even with the help of data augmentation techniques.

In the analysis of new structure 1230 by the lowest trained model, a new rank of the new structure 1230 may be estimated by weighting the distances and levels of all neighboring a priori ranked structures. Specifically, distances between new structure embedding 1230 and embeddings 1220, 1240, 1250, 1260, and 1270 of the five ranked structures may be determined, and ranked structures in the vicinity (within a threshold distance in the output space) of the new structure embedding 1230 may be identified. In this example, the ranked structures in the vicinity of the new structure include embeddings 1220, 1240, 1250, and 1270, and the ranked structures in the vicinity are represented via connecting dashed lines in this example map 1200. Further, weightage may be assigned to each of the selected ranked structures 1220, 1240, 1250, and 1270 based on their respective distances from the new structure embedding 1230. Furthermore, the new rank of the new structure 1230 may be determined based on weighted distances and the levels of all neighboring a priori ranked structures.

In this exemplary case, the new rank of the new structure may have a value about 1.5. Further, it will appreciated that a priori structure ranking can be disease specific, and this can serve as additional a priori information.

FIG. 13 is a block diagram of a nuclear medicine imaging system 1300 constructed in accordance with various embodiments, which in this embodiment is a single-photon emission computed tomography (SPECT) imaging system. It should be noted that the imaging system may also be a multi-modality imaging system, such as an NM/CT imaging system. The imaging system 1300, illustrated as a SPECT imaging system, generally includes, a gantry 12 and a rotor 14 that is oriented about a gantry central bore 16. The rotor 14 is configured to support one or more NM pixelated cameras 18 and 20.

A patient table 24 is configured to facilitate ingress and egress of a patient 25 into an examination position that is substantially aligned with the examination axis 22. During an imaging scan, the patient table 24 may be controlled by a table controller unit 202 to move the patient table 24 axially into and out of the bore 16. In one embodiment, the imaging system 1300 also includes the proximity detection system (PDS) module 116. In operation, the PDS module 116 facilitates maintaining the gamma cameras 18 and 20 in relatively close proximity to a region of interest, such as for example, a patient being imaged without contacting the patient or each other. Accordingly, the PDS may include a first patient safety device or sensor array 1310 and a second patient safety device or sensor array 1312. The outputs from the sensor arrays 1310 and 1312 are input to a processing unit 1314.

The gamma cameras 18 and 20 may be located at multiple positions (e.g., in an L-mode configuration) with respect to the patient 25. It should be noted that the gamma cameras 18 and 20 are configured for movable operation along (or about) the gantry 12. The table controller unit 202 may control the movement and positioning of the patient table 24 with respect to the gamma cameras 18 and 20 with respect to the patient 25 to position the desired anatomy of the patient 25 within the fields of view (FOVs) of the gamma cameras 18 and 20, which may be performed prior to acquiring an image of the anatomy of interest.

A controller unit 1320 includes the table controller 1322 and a gantry motor controller 1324 that each may be automatically commanded by the processing unit 1314, manually controlled by an operator, or a combination thereof. The table controller 1322 may move the patient table 24 to position the patient 25 relative to the FOV of the gamma cameras 18 and 20. The imaging data may be combined and reconstructed into an image, which may comprise 2D images, a 3D volume, or a 3D volume over time (4D).

A data acquisition system (DAS) 1330 receives analog and/or digital electrical signal data produced by the gamma cameras 18 and 20 and decodes the data for subsequent processing as described in more detail herein. An image reconstruction processor 1332 receives the data from the DAS 1330 and reconstructs an image using any reconstruction process known in the art. A data storage device 1334 may be provided to store data from the DAS 1330 and/or reconstructed image data. An input device 1336 may also be provided to receive user inputs and a display 1338 may be provided to display reconstructed images.

The processing unit 1314 may include a processor, such as processor 104 at FIG. 1. The processing unit 1314 may store a deep learning module configured with a deep learning model for learning base structure similarity by training of a plurality of neural network models with a plurality of training data sets, each with a different perturbation level, as discussed above with respect to FIGS. 1-12. Upon training, the deep learning model may be implemented to evaluate structural similarity between at least a baseline image and a follow-up image, each acquired by imaging system 1300, during functional imaging medical scan with the imaging system 1300. While the present example illustrates the deep learning model implemented by processing unit 104, it will be appreciated that the model may be implemented by an edge device connected to the processing unit, a cloud in communication with the processing unit, or any appropriate combination thereof. Further, it will be appreciated that the deep learning model may be implemented by any processor associated with other imaging modalities such as MM system, CT system, X-ray system, PET system, SPECT system, ultrasound system, etc. for structural comparison between at least two anatomical or physiological process structures, or for structural comparison of an anatomical or physiological process structure with one or more known a priori ranked structural types as discussed herein. If only one new structure is provided, the similarity index can be identified based on the one or more a priori ranked structures.

The technical effect of training a deep learning model having a plurality of neural network models with each of a plurality of training data sets, each having a different perturbation level is efficient and accurate training of the deep learning model without relying on large clinical data sets. Another technical effect of implementing the deep learning model is obtaining a more accurate similarity ranking based on structural comparison of at least two scan images. Yet another technical effect of implementing the deep learning model is obtaining a comprehensive evaluation, including a structural comparison and a statistical comparison, between at least two medical scan images. A further technical effect of implementing the deep learning model is determination of a direction of change in a medical condition under evaluation. An additional technical effect of implementing the deep learning model is more accurate evaluation of a disease or physiological condition based on determination of an amount of structural change between a first and second medical image of an anatomical structure or a physiological process signal.

An embodiment for a method includes generating a standardized similarity score based on a comparison of a first and second medical image of a lesion, the similarity score standardized based on a degree of perturbation of a plurality of base structures that corresponds to a change between the first and second medical images; wherein the plurality of base structures are subject to perturbation by a perturbation algorithm. A first example of the method includes wherein the plurality of base structures include synthetic base structures generated by the perturbation algorithm. In a second example of the method, which optionally includes the first example, and further includes wherein the degree of perturbation is based on one or more of structural variations and image quality variations of the plurality of base structures. In a third example of the method, which optionally includes one or both of the first and second examples, the method further includes wherein the structural variations include one or more of a linear translation of the plurality of base structures along one or more random axes, a rotation of the plurality of base structures along one or more rotation axes, a resizing factor applied to the plurality of base structures, and wherein the image quality variations include added image noise. In a fourth example of the method, which optionally includes one or more or each of the first through third examples, the method further includes wherein the perturbation algorithm includes training each of a plurality of neural network models with a different degree of perturbations of the plurality of base structures. In a fifth example of the method, which optionally includes one or more or each of the first through fourth examples, the method further includes wherein each of the plurality of neural network models are constructed based on a same network architecture, and wherein the same network architecture is any of a siamese network architecture, a triplet network architecture, a prototypical network architecture, a relation network architecture, and a matching network architecture. In a sixth example of the method, which optionally includes one or more or each of the first through fifth examples, the method includes wherein determining the degree of perturbation that corresponds to the change between the first and second medical images includes selecting a desired neural network model trained with a lowest degree of perturbation and where, in a desired output space of the desired neural network model, a distance between the first and second medical image mappings of the lesion is equal to or smaller than a corresponding mean distribution size of one or more neighboring base structures identified in a vicinity of the first and second medical image mappings of the lesion. In a seventh example of the method, which optionally includes one or more or each of the first through sixth examples, the method further includes determining a statistical value change of radiotracer uptake activities between the first and second medical image of the lesion, and calculating a combined similarity metric based on the standardized similarity score and the statistical value change. In an eighth example of the method, which optionally includes one or more or each of the first through seventh examples, the method further includes wherein the combined similarity metric is based on assigning weightages to the standardized similarity score and the statistical value change, the weightages based on a disease condition associated with the lesion.

An embodiment is directed to a method for structural comparison in functional medical imaging, comprising: receiving a baseline medical scan image and a follow-up medical scan image; inputting the baseline medical scan image and the follow-up medical scan image into a trained deep learning model, the trained deep learning model including a plurality of neural network models, each of the plurality of neural network models trained with a corresponding training set from a plurality of training set of base structures, each having a different perturbation level; and determining a structural similarity metric between the baseline medical image and the follow-up medical image based on a baseline embedding of the baseline medical scan image, a follow-up embedding of the follow-up scan image, and a distribution of base structure embeddings in corresponding output space of each of the plurality of trained neural networks. A first example of the method includes wherein determining the structural similarity metric includes identifying one or more neural network models from the plurality of neural network models where a corresponding distance between the corresponding baseline and the follow-up embeddings is equal to or smaller than a corresponding mean distribution size of one or more neighboring base structures identified in a vicinity of the corresponding baseline and follow-up embeddings; selecting a desired neural network model from the one or more neural network model, where the desired neural network model is trained with a lowest training data set having a lowest degree of perturbation; and determining a similarity index between the baseline image and the follow-up image based on the lowest degree of perturbation. In a second example of the method, which optionally includes the first example, and further includes wherein each of the plurality of training data sets are derived from an un-perturbed set including a plurality of un-perturbed base structures; and wherein the different perturbation level of each of the plurality of training data sets is adjusted based on a first standard deviation of a first distribution of linear translation of one or more of the plurality of un-perturbed base structures along one or more random axes, a second standard deviation of a second angular distribution of small rotations one or more of the plurality of un-perturbed base structures along one or more random angular axes, a third standard deviation of a third distribution of a resizing factor of one or more of the plurality of un-perturbed base structures, and a fourth standard deviation of a Gaussian noise factor added to the plurality of un-perturbed base structures. In a second example of the method, which optionally includes the first example, and further includes determining a statistical value change of radiotracer uptake activities between the baseline medical scan image and the follow-up medical scan image, and calculating a combined similarity metric based on the structural similarity metric and the statistical value change. In a third example of the method, which optionally includes one or both of the first and second examples, and further includes outputting one or more of a first indication of a rank of similarity and a second indication of a direction of change between the baseline and the follow-up images based on the structural similarity metric. In a fourth example of the method, which optionally includes one or more or each of the first through third examples, the method further includes wherein each of the plurality of neural network models are constructed based on a same network architecture.

An embodiment for a system for structural comparison in medical imaging is provided. The system includes a memory storing a deep learning model, the deep learning model including a plurality of neural network models; and a processor communicably coupled to the memory and configured to: during a data set generation process, generate a plurality of training data sets from an un-perturbed set of base structures, each of the plurality of training data sets having a different perturbation level of the un-perturbed set of base structures; during a training process, train each of the plurality of neural network models with a corresponding set from the plurality of training data sets with respect to the un-perturbed set of base structures to generate corresponding mappings of the base structures and its corresponding perturbations in each output space of each of the plurality of neural network models; and during an inference process, input at least two medical scan images including a baseline scan image and a follow-up scan image, into each of the plurality of trained neural network models, and evaluate the baseline scan image and the follow-up scan image in each output space of each of the plurality of neural network models based on a baseline scan image mapping, a follow-up scan image mapping, and the corresponding mappings of the base structures and its corresponding perturbations in each output space of each of the plurality of neural network models. In a first example of the system, a level of perturbation of the un-perturbed set of base structures is based on one or more of structural variations and image quality variations. In a second example of the imaging system, which optionally includes the first example, each of the plurality of neural networks are constructed with a same type of convolutional neural network architecture. In a third example of the imaging system, which optionally includes one or both of the first and second examples, evaluating the baseline scan image and the follow-up scan image includes selecting a desired neural network model trained with a corresponding training set having a degree of perturbation corresponding to a structural variation between the baseline and the follow-up scan images, and ranking structural similarity between the baseline and follow-up images based on the selected neural network model. In a fourth example of the imaging system, which optionally includes one or more or each of the first through third examples, the same type of convolutional neural network architecture is any of a siamese network architecture, a triplet network architecture, a prototypical network architecture, a relation network architecture, and a matching network architecture.

One or more specific embodiments of the present disclosure are described above in order to provide a thorough understanding. These described embodiments are only examples of systems and methods for evaluating structural similarity between at least two anatomical structures by using a deep learning model implementing a plurality of neural network models. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements.

The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
    generating a standardized similarity score based on a comparison of a first and second medical image of a lesion, the similarity score standardized based on a degree of perturbation of a plurality of base structures that corresponds to a change between the first and second medical images; wherein the plurality of base structures are subject to perturbation by a perturbation algorithm, wherein the perturbation algorithm includes training at least one neural network model with at least a first degree of perturbation of the plurality of base structures.

2. The method of claim 1, wherein the plurality of base structures include synthetic base structures generated by the perturbation algorithm.

3. The method of claim 1, wherein the degree of perturbation is based on one or more of structural variations and image quality variations of the plurality of base structures.

4. The method of claim 3, wherein the structural variations include one or more of a linear translation of the plurality of base structures along one or more random axes, a rotation of the plurality of base structures along one or more rotation axes, a resizing factor applied to the plurality of base structures, and wherein the image quality variations include added image noise.

5. The method of claim 1, wherein the perturbation algorithm includes training each of a plurality of neural network models with a different degree of perturbations of the plurality of base structures.

6. The method of claim 5, wherein each of the plurality of neural network models are constructed based on a same network architecture, and wherein the same network architecture is any of a siamese network architecture, a triplet network architecture, a prototypical network architecture, a relation network architecture, and a matching network architecture.

7. The method of claim 5, wherein determining the degree of perturbation that corresponds to the change between the first and second medical images includes selecting a desired neural network model trained with a lowest degree of perturbation and where, in a desired output space of the desired neural network model, a distance between a first and second medical image mappings of the lesion is equal to or smaller than a corresponding mean distribution size of one or more neighboring base structures identified in a vicinity of the first and second medical image mappings of the lesion.

8. The method of claim 1, further comprising determining a statistical value change of radiotracer uptake activities between the first and second medical image of the lesion, and calculating a combined similarity metric based on the standardized similarity score and the statistical value change.

9. The method of claim 8, wherein the combined similarity metric is based on assigning weightages to the standardized similarity score and the statistical value change, the weightages based on a disease condition associated with the lesion.

10. A method for structural comparison in functional medical imaging, comprising:
    receiving a baseline medical scan image and a follow-up medical scan image;
    inputting the baseline medical scan image and the follow-up medical scan image into a trained deep learning model, the trained deep learning model including a plurality of neural network models, each of the plurality of neural network models trained with a corresponding training set from a plurality of training set of base structures, each having a different perturbation level; and
    determining a structural similarity metric between the baseline medical image and the follow-up medical image based on a baseline embedding of the baseline medical scan image, a follow-up embedding of the follow-up scan image, and a distribution of base structure embeddings in corresponding output space of each of the plurality of trained neural networks.

11. The method of claim 10, wherein determining the structural similarity metric includes identifying one or more neural network models from the plurality of neural network models where a corresponding distance between the corresponding baseline and the follow-up embeddings is equal to or smaller than a corresponding mean distribution size of one or more neighboring base structures identified in a vicinity of the corresponding baseline and follow-up embeddings; selecting a desired neural network model from the one or more neural network model, where the desired neural network model is trained with a lowest training data set having a lowest degree of perturbation; and determining a similarity index between the baseline image and the follow-up image based on the lowest degree of perturbation.

12. The method of claim 10, wherein each of the plurality of training data sets are derived from an un-perturbed set including a plurality of un-perturbed base structures; and wherein the different perturbation level of each of the plurality of training data sets is adjusted based on a first standard deviation of a first distribution of linear translation of one or more of the plurality of un-perturbed base structures along one or more random axes, a second standard deviation of a second angular distribution of small rotations one or more of the plurality of un-perturbed base structures along one or more random angular axes, a third standard deviation of a third distribution of a resizing factor of one or more of the plurality of un-perturbed base structures, and a fourth standard deviation of a Gaussian noise factor added to the plurality of un-perturbed base structures.

13. The method of claim 11, further comprising determining a statistical value change of radiotracer uptake activities between the baseline medical scan image and the follow-up medical scan image, and calculating a combined similarity metric based on the structural similarity metric and the statistical value change.

14. The method of claim 10, further comprising outputting one or more of a first indication of a rank of similarity and a second indication of a direction of change between the baseline and the follow-up images based on the structural similarity metric.

15. The method of claim 10, wherein each of the plurality of neural network models are constructed based on a same network architecture.

16. A system for structural comparison in medical imaging comprising:
 a memory storing a deep learning model, the deep learning model including a plurality of neural network models; and
 a processor communicably coupled to the memory and configured to:
  during a data set generation process, generate a plurality of training data sets from an un-perturbed set of base structures, each of the plurality of training data sets having a different perturbation level of the un-perturbed set of base structures;
  during a training process, train each of the plurality of neural network models with a corresponding set from the plurality of training data sets with respect to the un-perturbed set of base structures to generate corresponding mappings of the base structures and its corresponding perturbations in each output space of each of the plurality of neural network models; and
  during an inference process,
   input at least two medical scan images including a baseline scan image and a follow-up scan image, into each of the plurality of trained neural network models, and
   evaluate the baseline scan image and the follow-up scan image in each output space of each of the plurality of neural network models based on a baseline scan image mapping, a follow-up scan image mapping, and the corresponding mappings of the base structures and its corresponding perturbations in each output space of each of the plurality of neural network models.

17. The system of claim 16, wherein a level of perturbation of the un-perturbed set of base structures is based on one or more of structural variations and image quality variations.

18. The system of claim 16, wherein each of the plurality of neural networks are constructed with a same type of convolutional neural network architecture.

19. The system of claim 18, wherein evaluating the baseline scan image and the follow-up scan image includes selecting a desired neural network model trained with a corresponding training set having a degree of perturbation corresponding to a structural variation between the baseline and the follow-up scan images, and ranking structural similarity between the baseline and follow-up images based on the selected neural network model.

20. The system of claim 18, wherein the same type of convolutional neural network architecture is any of a siamese network architecture, a triplet network architecture, a prototypical network architecture, a relation network architecture, and a matching network architecture.

* * * * *